US012275711B2

(12) United States Patent
Opatz et al.

(10) Patent No.: US 12,275,711 B2
(45) Date of Patent: Apr. 15, 2025

(54) COMPOUNDS HAVING EXCITED STATE INTRAMOLECULAR PROTON TRANSFER (ESIPT) CHARACTER FOR USE IN TREATING AND/OR PREVENTING SUNBURN AND/OR PREVENTING U.V. DAMAGE

(71) Applicants: UNIVERSITY OF THE WITWATERSRAND, JOHANNESBURG, Johannesburg (CA); JOHANNES GUTENBERG UNIVERSITY, Mainz (DE)

(72) Inventors: Till Opatz, Mainz (DE); Jonas Kühlborn, Mainz (DE); Charles B. De Koning, Johannesburg (ZA); Kennedy J. Ngwira, Johannesburg (ZA); Quintino A. Mgani, Johannesburg (ZA)

(73) Assignees: UNIVERSITY OF THE WITWATERSRAND, JOHANNESBURG, Johannesburg (ZA); JOHANNES GUTENBERG UNIVERSITY, Mainz (DE)

( * ) Notice: Subject to any disclaimer, the term of this patent is extended or adjusted under 35 U.S.C. 154(b) by 759 days.

(21) Appl. No.: 17/437,519

(22) PCT Filed: Mar. 12, 2020

(86) PCT No.: PCT/IB2020/052254
§ 371 (c)(1),
(2) Date: Sep. 9, 2021

(87) PCT Pub. No.: WO2020/183422
PCT Pub. Date: Sep. 17, 2020

(65) Prior Publication Data
US 2022/0144785 A1    May 12, 2022

(30) Foreign Application Priority Data
Mar. 12, 2019   (ZA) ................................ 2019/01514

(51) Int. Cl.
C07D 251/14    (2006.01)
A61K 8/35    (2006.01)
A61K 8/49    (2006.01)
A61Q 17/04    (2006.01)
C07C 65/40    (2006.01)
C07D 271/107    (2006.01)
C07D 309/12    (2006.01)

(52) U.S. Cl.
CPC .............. *C07D 251/14* (2013.01); *A61K 8/35* (2013.01); *A61K 8/49* (2013.01); *A61K 8/4966* (2013.01); *A61K 8/498* (2013.01); *A61Q 17/04* (2013.01); *C07C 65/40* (2013.01); *C07D 271/107* (2013.01); *C07D 309/12* (2013.01)

(58) Field of Classification Search
CPC .............. C07D 251/14; C07D 271/107; C07D 309/12; A61K 8/35; A61K 8/49; A61K 8/4966; A61K 8/498; A61Q 17/04; C07C 65/40
USPC ......................................................... 514/241
See application file for complete search history.

(56) References Cited

FOREIGN PATENT DOCUMENTS

WO    2013/026727 A1    2/2013

OTHER PUBLICATIONS

ISR for International Application PCT/IB2020/052254 mailed Jul. 17, 2020.
Written Opinion for International Application PCT/IB2020/052254 mailed Jul. 17, 2020.

*Primary Examiner* — Kristin A Vajda
(74) *Attorney, Agent, or Firm* — LADAS & PARRY LLP

(57) ABSTRACT

This disclosure relates to use of cashew nut shell liquid (CNSL) phenolics in the manufacture of molecules having ESIPT character, wherein said molecules are UVA and/or UVB absorbers, and further wherein said molecules are formulated as protectants against UVA and/or UVB radiation. The disclosure extends to use of CNSL in the manufacture of compositions including molecules having ESIPT character for treating and/or preventing sunburn and/or preventing U.V. damage.

3 Claims, 9 Drawing Sheets

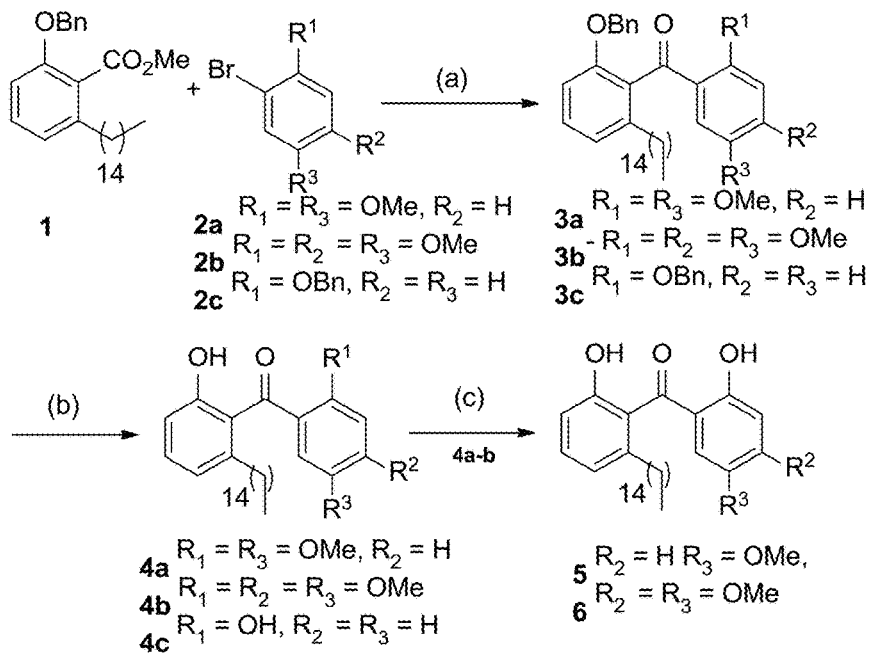
FIGURE 1 shows reagents and conditions: (a) n-BuLi, THF, -78 °C to rt, 2-24 h, 3a-c 10-47%; (b) Pd/C, $H_2$, MeOH, EtOAc, rt, 24 h, 4a-c, 84-99%; (c) For 4a: $AlCl_3$, pyridine, PhMe, reflux, 4d, 58%; For 4b: $BCl_3$, $CH_2Cl_2$, -78 °C to rt, 4 d, 69%.
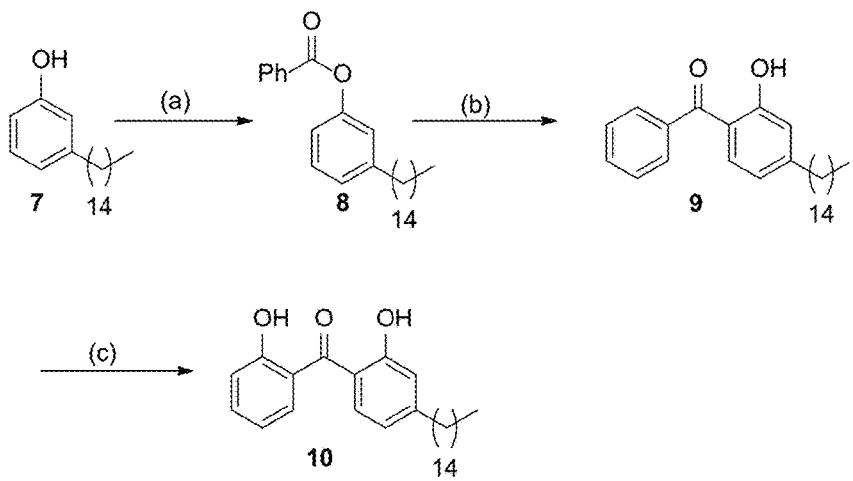
FIGURE 2 shows reagents and conditions: a) PhCOCl, DMAP, $Et_3N$, 2-Me-THF, 0° C to rt, 2 h, 89%; b) $AlCl_3$, PhCl, Mw (160 °C, 150 W, 30 min), 78%; c), [Ru(p-cymene)$Cl_2$]$_2$ (2.5 mol %), $K_2S_2O_8$, TFA/TFAA, 80° C, 14 h, 72%.

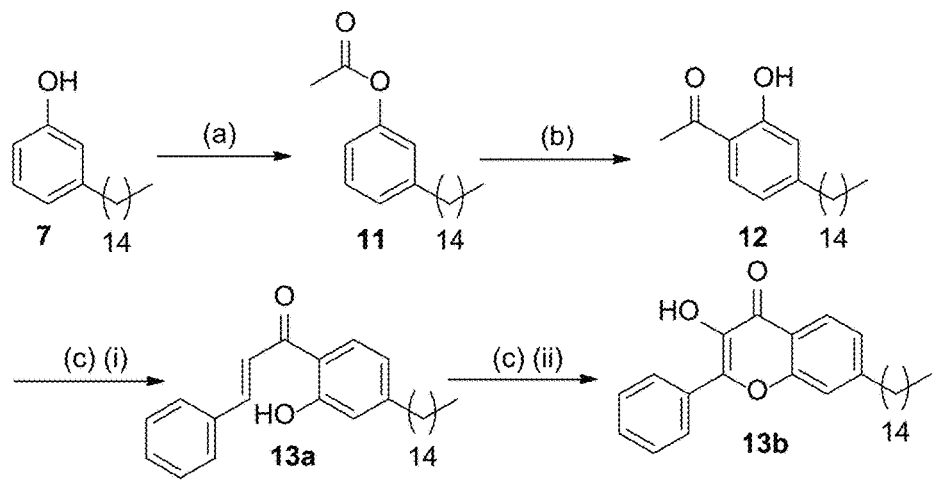

FIGURE 3 shows reagents and conditions: (a) CH₃COCl, DMAP, Et₃N, 2-Me-THF, 0 °C to rt, 2 h, 93%; (b) AlCl₃, PhCl, Mw (160 °C, 150 W, 30 min), quant. (c) (i) NaOH, PhCHO, MeOH, 3 h, 67% (ii) 0.5N aq. NaOH, H₂O₂, rt, 4 h, 88%.

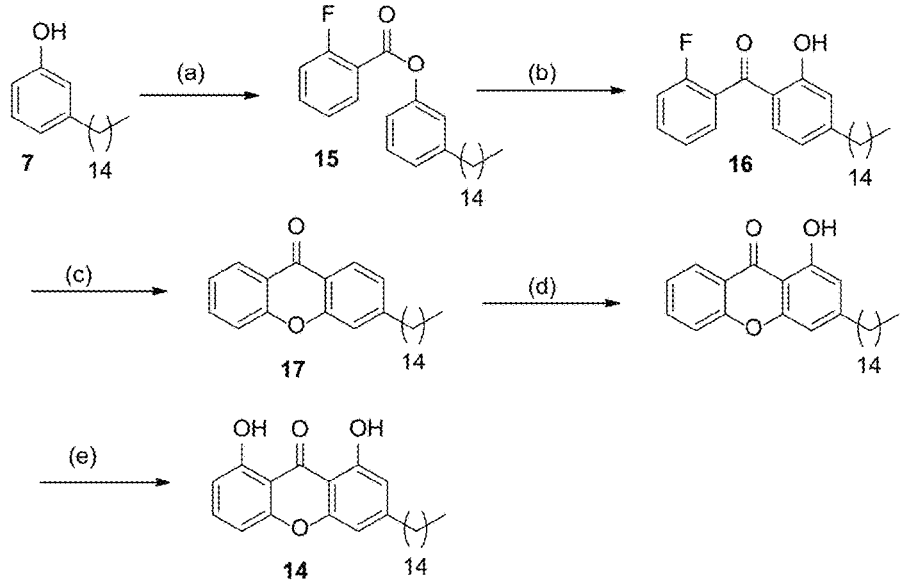

FIGURE 4 shows reagents and conditions: (a) 2-Flourobenzoyl chloride, DMAP, Et₃N, 2-Me-THF, 0 °C to rt, 3 h, quant.; (b) AlCl₃, PhCl, Mw (160 °C, 150 W), 30 min, 84%; (c) K₂CO₃, Me₂CO, reflux, 6 h, 86%; (d) [Ru(p-cymene)Cl₂]₂ (2.5 mol %), K₂S₂O₈, TFA/TFAA, 80 °C, 12 h, 71%; (e) [Ru(p-cymene)Cl₂]₂ (2.5 mol %), K₂S₂O₈, TFA/TFAA, 80 °C, 12 h, 64%.

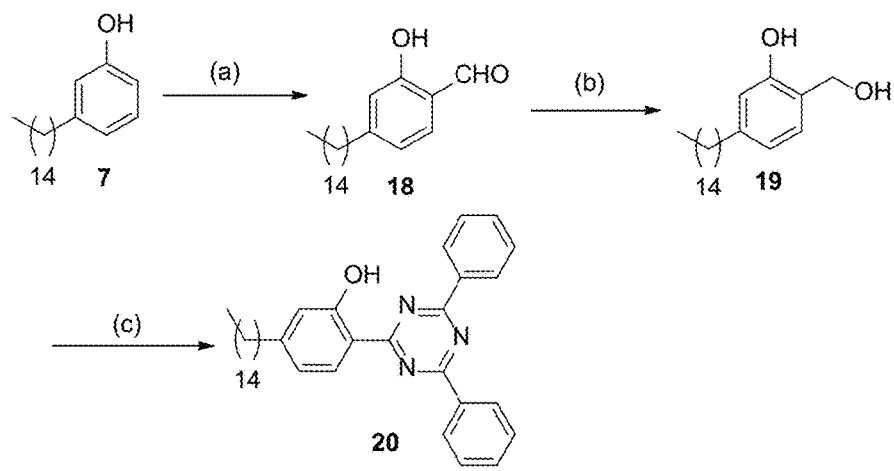
FIGURE 5 shows reagents and conditions: (a) SnCl$_4$, Bu$_3$N, (CH$_2$O)$_n$, PhMe, 100 °C, 18 h, 77%; (b) LiAlH$_4$, THF, rt, 6 h, 81%; Benzamidine hydrochloride, Cu(OAc)$_2$, Na$_2$CO$_3$, PhMe, 110 °C, 12 h, 62%.
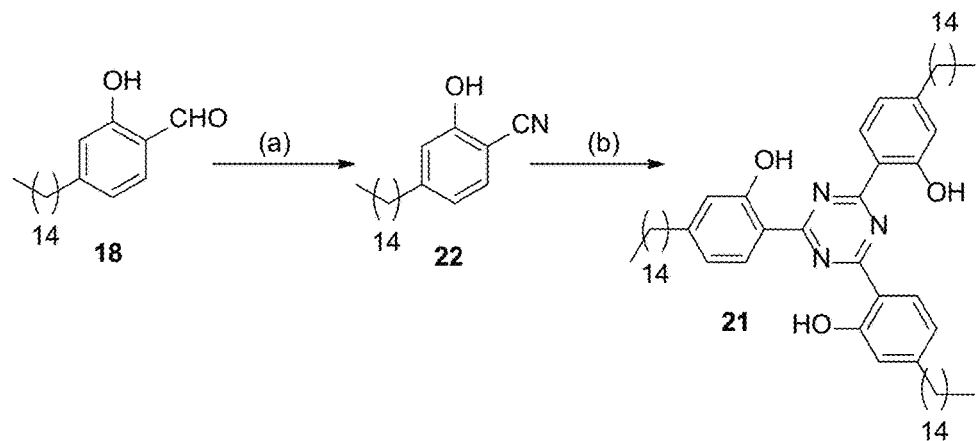
FIGURE 6 shows reagents and conditions: (a) NH$_2$OH·HCl, FeCl$_3$, DMF, reflux, 18 h, 80%; (b) Mw: 220 °C, 200 W, 1.5 h, neat, 73%.

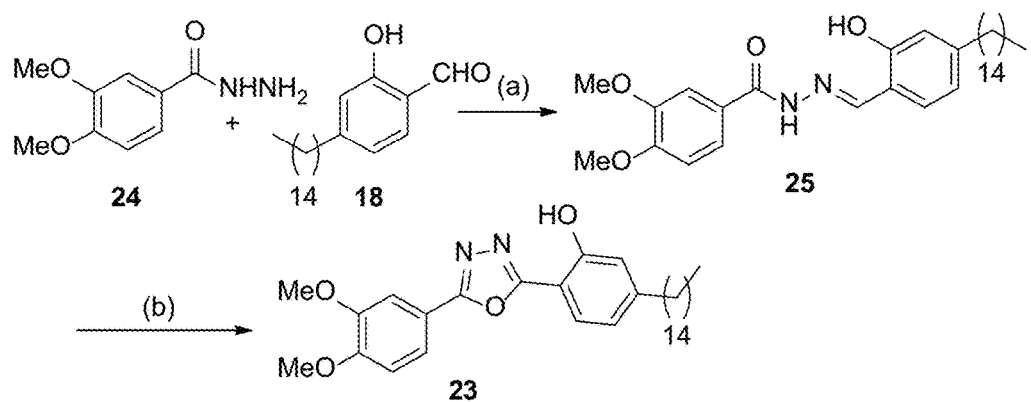
FIGURE 7 shows reagents and conditions: (a) Et₂O, MeOH, rt, 18 h, 82%; (b) PhI(OAc)₂, Me₂CO, rt, 5 h, 47%.

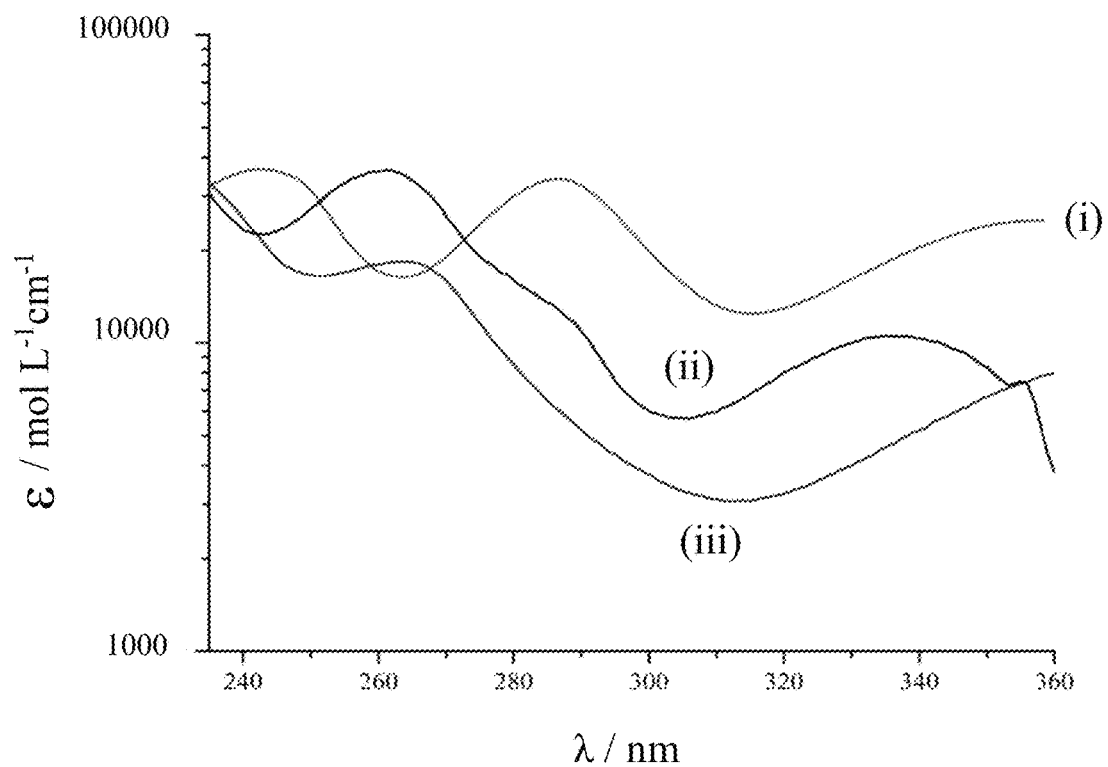
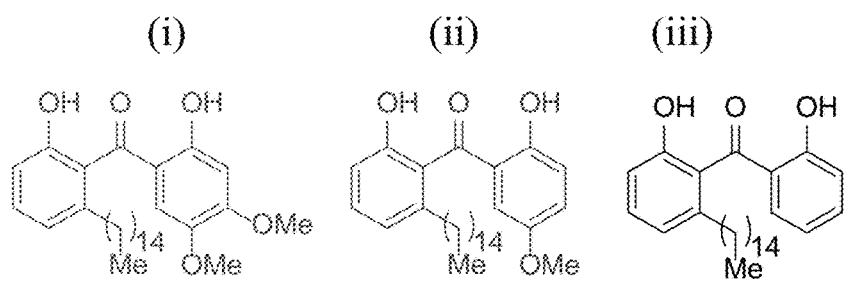
ε (358 nm) = 25014          ε (374 nm) = 8785          ε (335 nm) = 10538
ε (287 nm) = 34096          ε (264 nm) = 18439         ε (261 nm) = 36366
FIGURE 8    shows UV absorbance profiles of benzophenones 4c, 5 and 6 derived from anacardic acid.

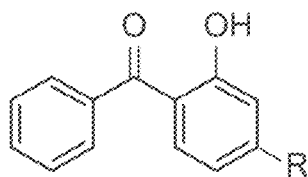 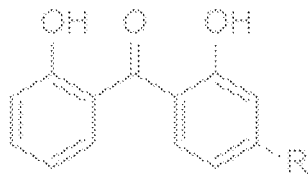
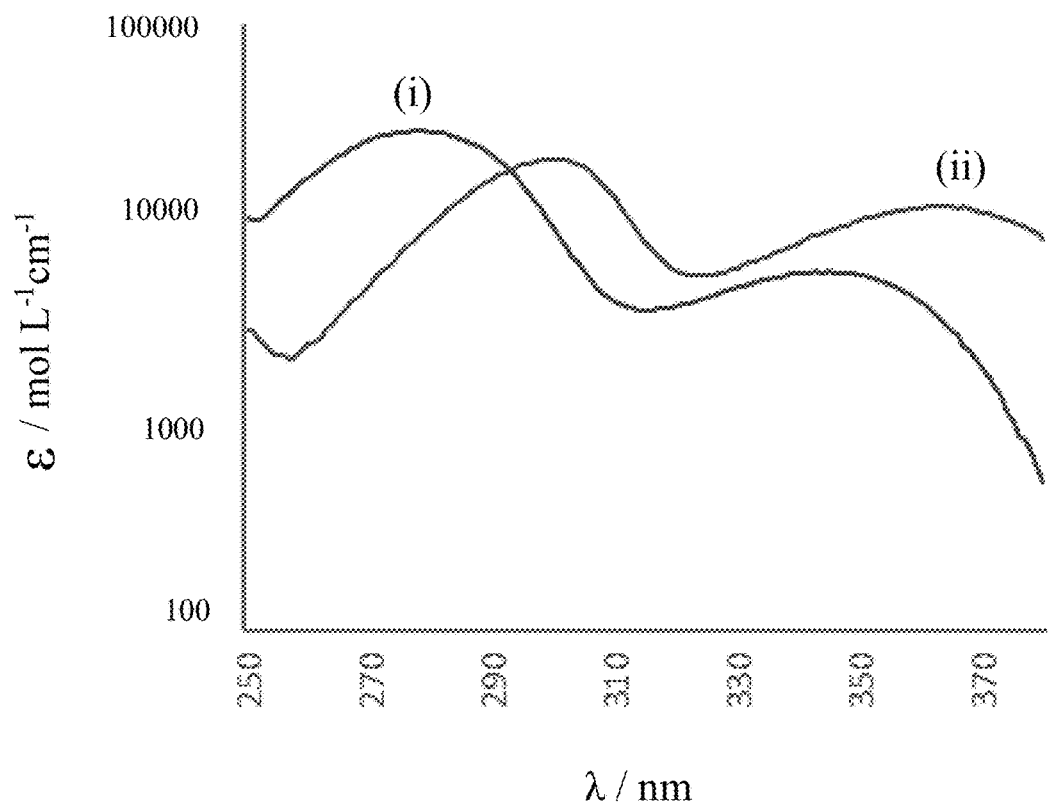
FIGURE 9 shows UV absorbance profiles of benzophenones 4c, 5 and 6 derived from cardanol.

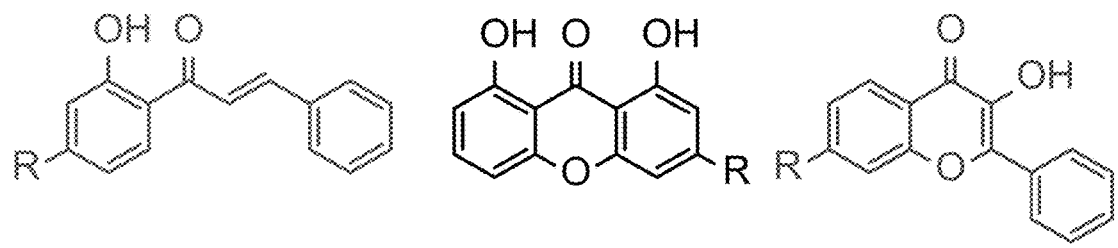
ε = 20,403 (314 nm)   ε = 23,765 (278 nm)   ε = 39,870 (314 nm)
ε = 10,250 (347 nm)   ε = 6,469 (323 nm)    ε = 44,979 (345 nm)
(i)                   (ii)                  (iii)
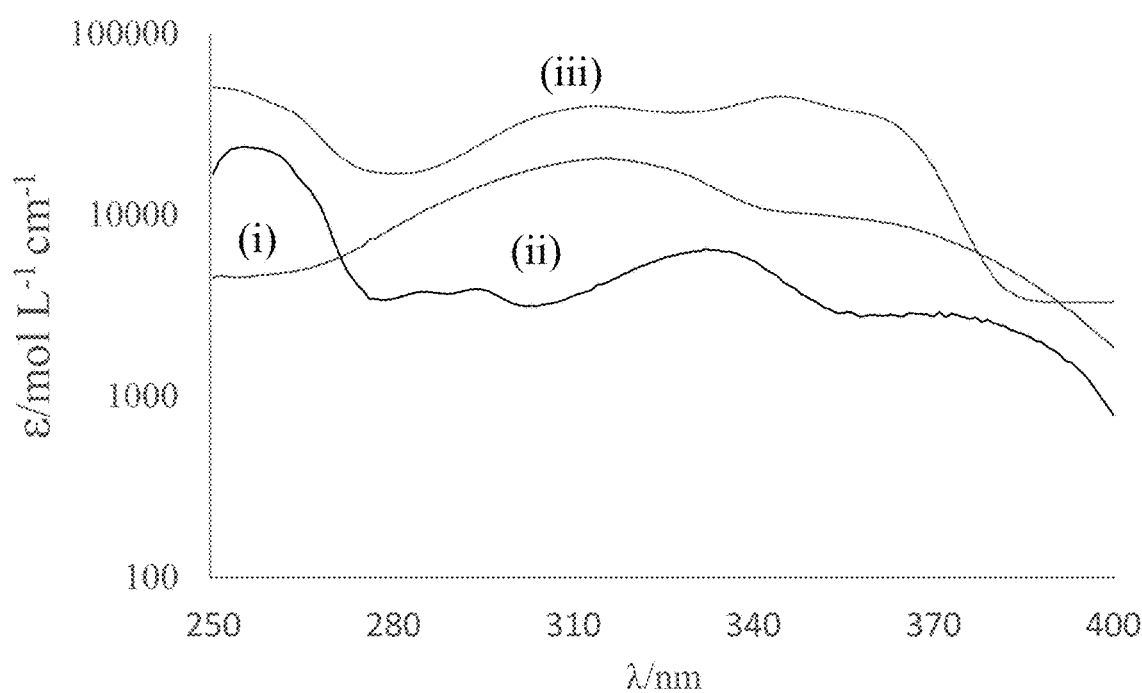
FIGURE 10    shows UV profiles of chalcone 13a, flavone 13b and xanthone 14.

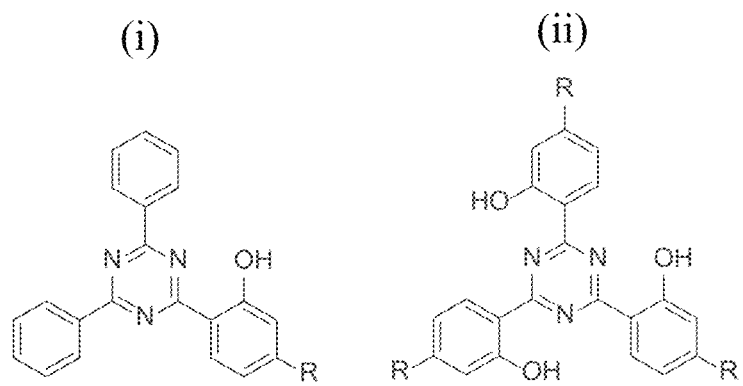
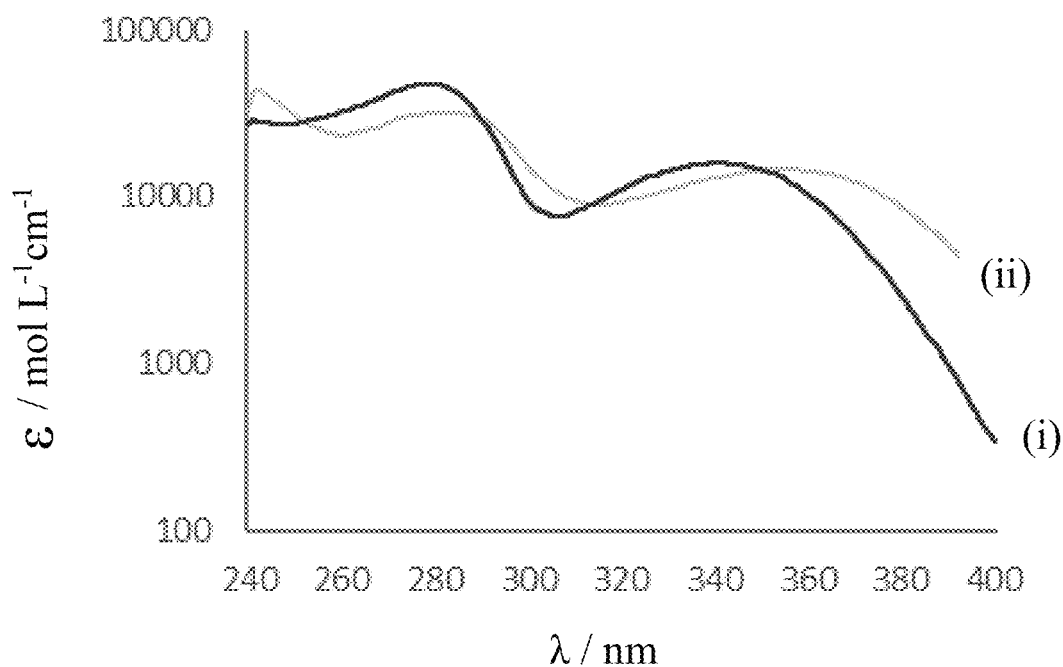
FIGURE 11 shows UV profiles of triazines 20 and 21

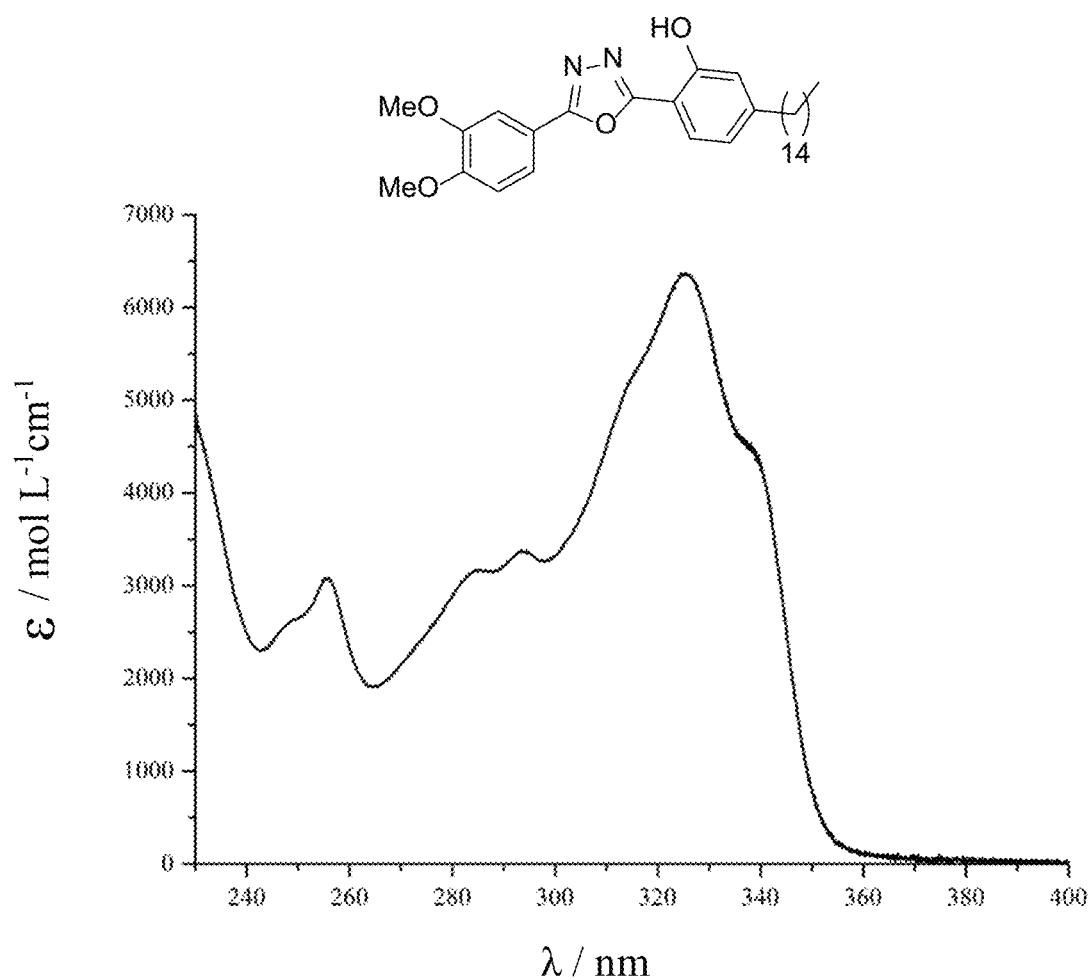
FIGURE 12 shows UV profiles of oxadiazole 23.

COMPOUNDS HAVING EXCITED STATE INTRAMOLECULAR PROTON TRANSFER (ESIPT) CHARACTER FOR USE IN TREATING AND/OR PREVENTING SUNBURN AND/OR PREVENTING U.V. DAMAGE

FIELD OF DISCLOSURE

This disclosure relates to the manufacture of molecules having excited state intramolecular proton transfer (ESIPT) character. Particularly, this disclosure relates to use of cashew nut shell liquid (CNSL) phenolics in the manufacture of molecules having ESIPT character, wherein said molecules are UVA and/or UVB absorbers, and further wherein said molecules are formulated as protectants against UVA and/or UVB radiation. The disclosure extends to use of CNSL in the manufacture of compositions including molecules having ESIPT character for treating and/or preventing sunburn and/or preventing U.V. damage.

This application is a national phase entry under 35 USC 371 of International Patent Application No.: PCT/IB2020/052254 filed on 12 Mar. 2020, which claims the benefit of ZA Application No. 2019/01514 filed on 12 March, the entire content of which is incorporated by reference.

BACKGROUND

Recently, there has been a move away from using petroleum or petroleum-based products as starting reagents in organic synthesis of commercially relevant chemical products. In order to employ sustainable carbon sources as starting reagents for organic synthesis researchers have considered the use of biomass, particularly non-edible biomass that would otherwise be discarded. As such, the valorization of non-edible biomass has been a much-researched topic.

One non-edible biomass source that has been a topic of much research is cashew nut shell liquid (CNSL). CNSL is known to have little commercial value on its own, however, CNSL is rich in phenolics and is known as a non-edible biomass-derived chemical feedstock for the production of paints, resins, polymers, and surfactants. Similarly, there has been a shift with consumers regarding willingness to purchase products not derived from sustainable sources, wherein consumers have become reluctant to purchase non-sustainably derived products.

Specifically within the healthcare and/or skincare sector as well as the materials protection sector there has been a significant drive towards providing for compositions and/or formulations that are not only derived from sustainable sources but are concomitantly innocuous to the human or animal, by way of example, being non-toxic; biodegradable; hypoallergenic; not capable of crossing the skin into tissue or bloodstream; not capable of disrupting hormones; and having few if any side reactions and/or side effects.

Conventional U.V. absorbers including sunscreens can generally be divided into two classes: (1) physical barriers (such as zinc oxide and titanium dioxide) and (2) chemical absorbers (such as oxybenzone, avobenzone and otisalate).

The physical barriers aim to block out ultraviolet (UV) radiation. Chemical absorbers absorb UV radiation. It has been shown from a quantum mechanical point of view, that the resonance energy of electron delocalization in aromatic compounds is in the same order of magnitude as the energy of radiation quanta present in the UVA and/or UVB region of the spectrum. Consequently, UVA and/or UVB radiation may readily cause a photochemical excitation of the chemical absorber sunscreen.

By absorbing UV-radiation, the absorber molecule is excited into a higher energy state ($S_1$ or $T_1$) from its ground state ($S_0$). As the sunscreen molecule returns to the ground state, light of longer wavelength is emitted that is lower in energy relative to the U.V. radiation. Alternatively, radiationless processes can occur, which only release heat instead of visible light.

In general, the absorption of light of short wavelengths can cause molecules to react photochemically, for example a cis-trans and/or E-Z photochemical isomerisation. Following a cis-trans and/or E-Z photochemical isomerisation, possible stereoselective metabolism may negatively influence pharmacokinetics, pharmacodynamics and toxicity, and should be avoided. Similarly, unwanted side reactions may take place. Radiation related mechanisms are possibly harmful not only causing skin irritation but also producing unwanted side reactions, and possible breakdown of chemical compounds into toxic constituents. There is a need for chemical UV absorbers developed from sustainable feedstock that at least ameliorate some of the disadvantages described herein or known in the prior art.

SUMMARY

In accordance with a first aspect of this disclosure there is provided a compound having excited state intramolecular proton transfer (ESIPT) character, said compound being at least one selected from the following group.

(i).

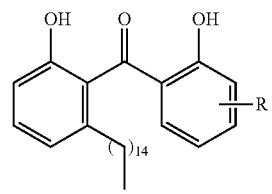

(For example, Compound 4c in the Description);

(ii).

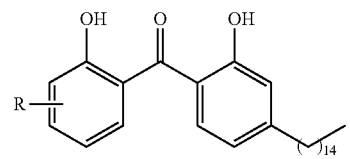

(For example, compound 10 in the Description);

(iii).

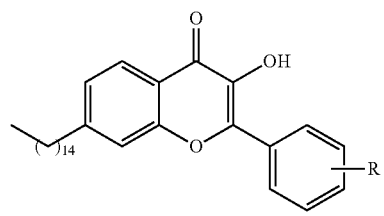

(For example, Compound 13b in the Description);

(iv).

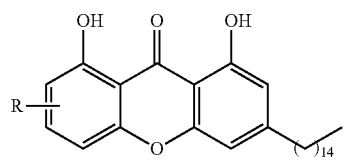

(For example, Compound 14 in the Description);

(v).

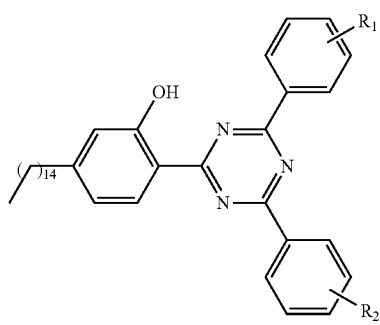

(For example, Compound 20 in the Description);

(vi).

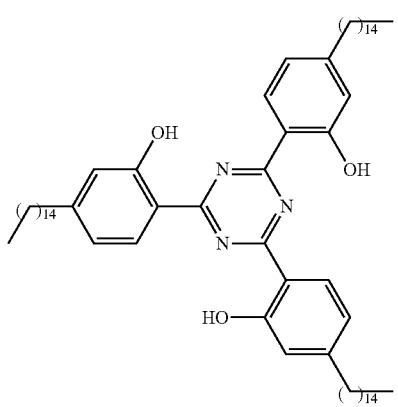

(Compound 21 in the Description), and (vii).

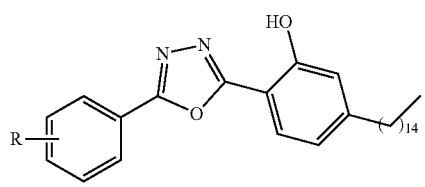

(For example, Compound 23 in the Description);
wherein for compounds (i) to (vii) R and/or $R_1$ and/or $R_2$ may each be at least one substituent or moiety located at one or more of an ortho, meta and/or para position on the benzene ring and may be selected from the group including: hydrogen, alkyl, alkenyl, alkynyl, cycloalkyl, cycloalkenyl, cycloalkynyl, aryl, heteroaryl, heteroalicyclyl, aralkyl, heteroalkyl, (heteroalicyclyl)alkyl, hydroxy, protected hydroxyl, alkoxy, aryloxy, acyl, mercapto, thioalkyl, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, nitrile, silyl, sulfenyl, sulfinyl, sulfonyl, haloalkyl, polyhaloalkyl, haloalkoxy, trihalomethanesulfonyl, trihalomethanesulfonamido, an amino, a mono-substituted amino and a di-substituted amino group, esters, alcohol, acetates and protected derivatives of any one of the aforementioned.

The compounds (i) to (vii) may be optionally substituted. One or more substituent R groups may be located at an ortho, meta and/or para position on an aromatic ring, typically a benzene ring. The ring may include more than one substituent R groups which may be the identical, or alternatively, may differ in chemical structure. The compounds (i) to (vii) may be optionally substituted with multiple R groups wherein the same R group or different R groups are linked or bonded forming chains or rings. Rings such as tetrahydronaphthalenyl groups may be formed.

In accordance with a second aspect of this disclosure there is provided any one or more of the compounds (i)-(vii) for use in the treatment and/or prevention of sunburn in a human or animal body, wherein compounds (i)-(vii) are:

(i).

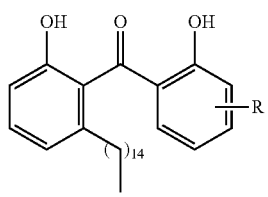

(For example, Compounds 4, 5 and 6 of the Description);

(ii).

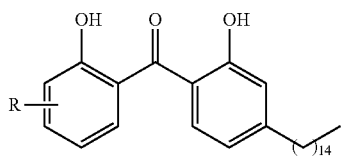

(For example, Compound 10 of the Description);

(iii).

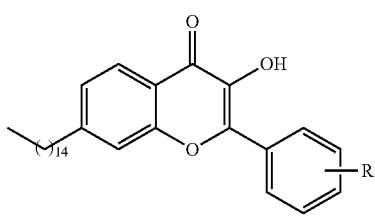

(For example Compound 13b of the Description);

(iv).

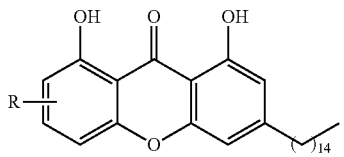

(For example Compound 14 of the Description):

(v).

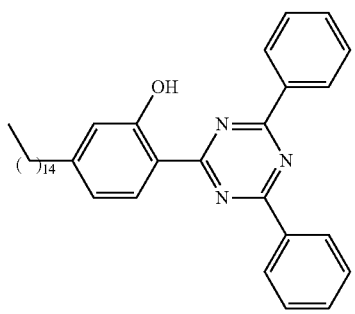

(For example Compound 20 of the Description);

(vi).

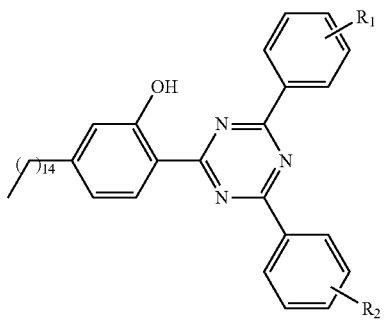

(For example, Compound 21 of the Description); and (vii).

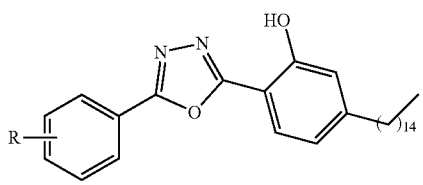

(For example, Compound 23 of the Description);

wherein for compounds (i) to (vii) R and/or $R_1$ and/or $R_2$ may each be at least one substituent or moiety located at one or more of an ortho, meta and/or para position on the benzene ring and may be selected from the group including: hydrogen, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, thioalkyl, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, nitrile, silyl, sulfenyl, sulfinyl, sulfonyl, haloalkyl, polyhaloalkyl, haloalkoxy, trihalomethanesulfonyl, trihalomethanesulfonamido, an amino, a mono-substituted amino and a di-substituted amino group, esters, alcohol, acetates and protected derivatives of any one of the aforementioned.

The compounds (i) to (vii) may be optionally substituted. One or more substituent R groups may be located at an ortho, meta and/or para position on an aromatic ring, typically a benzene ring. The ring may include more than one substituent R groups which may be the identical, or alternatively, may differ in chemical structure. The compounds (i) to (vii) may be optionally substituted with multiple R groups wherein the same R group or different R groups are linked or bonded forming chains or rings. Rings such as tetrahydronaphthalenyl groups may be formed.

The compounds may be formulated into compositions for use in the treatment and/or prevention of sunburn in the human or animal body, wherein the compositions may include at least one of, but not limited to, the following group: aqua, glycerine, trisodium ethylene diamine tetraacetic acid (EDTA), tocopheryl acetate, phenoxyethanol, cetyl alcohol, xantham gum, polyethylene glycol (PEG), sodium cetearyl sulphate, glycerol stearate, and parfum.

The Applicant surprisingly found that the compounds (i) to (vii) were UVA and UVB absorbers that did not show radiation related deactivation. The compounds did not undergo any cis-trans and/or E-Z isomerization nor decompose into harmful substituents. Surprisingly, the Applicant has found that compounds (i) to (vii) dissipate UV radiation through an efficient radiationless deactivation process by means of rapid tautomerization which proceeds via the excited-state intramolecular proton transfer (ESIPT) mechanism. Compounds (i) to (vii) for use in the treatment and/or prevention of sunburn surprisingly ameliorates at least some of the disadvantages known from the prior art.

In accordance with a third aspect of this disclosure there is provided use of any one or more of the compounds according to the second aspect of this disclosure in the manufacture of a medicament for the treatment and/or prevention of sunburn in a human or animal body.

In accordance with a fourth aspect of this disclosure there is provided a compound having excited state intramolecular proton transfer (ESIPT) character, produced from cashew nut shell liquid (CNSL) for use in the treatment and/or prevention of sunburn in a human or animal body.

The compounds may be any one or more of the compounds according to the second aspect of this disclosure.

The compounds may be formulated into compositions for use in the treatment and/or prevention of sunburn in the human or animal body, wherein the compositions may include at least one of, but not limited to, the following group: aqua, glycerine, trisodium ethylene diamine tetraacetic acid (EDTA), tocopheryl acetate, phenoxyethanol, cetyl alcohol, xantham gum, polyethylene glycol (PEG), sodium cetearyl sulphate, glycerol stearate, and parfum.

In accordance with a fifth aspect of this disclosure there is provided use of cashew nut shell liquid (CNSL) for manufacturing a compound having excited state intramolecular proton transfer (ESIPT) character, wherein said compound is for the treatment and/or prevention of sunburn in a human or animal body.

The compounds may be any one or more of the compounds according to the second aspect of this disclosure.

The compounds may be formulated into compositions for use in the treatment and/or prevention of sunburn in the human or animal body, wherein the compositions may include at least one of, but not limited to, the following group: aqua, glycerine, trisodium ethylene diamine tetra-acetic acid (EDTA), tocopheryl acetate, phenoxyethanol, cetyl alcohol, xantham gum, polyethylene glycol (PEG), sodium cetearyl sulphate, glycerol stearate, and parfum.

In accordance with a sixth aspect of this disclosure there is provided a method of manufacturing a compound having excited state intramolecular proton transfer (ESIPT) character, said method comprising the following steps:

(a), isolating phenolic compounds from cashew nut shell liquid (CNSL), preferably said phenolic compounds including at least one of but not limited to the following group: anacardic acid, cardol and cardanol;

(b), transforming said isolated phenolic compound into any one or more of the compounds according to the second aspect of this disclosure.

The method may include one or more steps as described and/or exemplified herein below.

In accordance with a seventh aspect of this disclosure there is provided a compound having excited state intramolecular proton transfer (ESIPT) character manufactured according to the method of the sixth aspect of this disclosure.

The compound may be any one or more of the compounds according to the first aspect of this disclosure.

The compounds may be formulated into compositions for use in the treatment and/or prevention of sunburn in the human or animal body, wherein the compositions may include at least one of, but not limited to, the following group: aqua, glycerine, trisodium ethylene diamine tetra-acetic acid (EDTA), tocopheryl acetate, phenoxyethanol, cetyl alcohol, xantham gum, polyethylene glycol (PEG), sodium cetearyl sulphate, glycerol stearate, and parfum.

In accordance with an eighth aspect of this disclosure there is provided a method of treating and/or preventing sunburn comprising application of a compound having excited state intramolecular proton transfer (ESIPT) character produced from cashew nut shell liquid (CNSL), as per the second aspect of this disclosure, onto a human or animal body.

The compounds may be any one or more of the compounds according to the second aspect of this disclosure.

The compounds may be formulated into compositions for use in the treatment and/or prevention of sunburn in the human or animal body, wherein the compositions may include at least one of, but not limited to, the following group: aqua, glycerine, trisodium ethylene diamine tetra-acetic acid (EDTA), tocopheryl acetate, phenoxyethanol, cetyl alcohol, xantham gum, polyethylene glycol (PEG), sodium cetearyl sulphate, glycerol stearate, and parfum.

In accordance with a ninth aspect of this disclosure there is provided an ultraviolet absorber and protectant composition comprising a compound having excited state intramolecular proton transfer (ESIPT) character produced from cashew nut shell liquid (CNSL).

The compounds may be as per the first or second aspects of this disclosure.

The ultraviolet absorber composition may include any one or more of the compounds according to the second aspect of this disclosure.

The ultraviolet absorber and protectant composition may be formulated as a sunscreen and may include at least one of, but not limited to, the following group: aqua, glycerine, trisodium ethylene diamine tetra-acetic acid (EDTA), tocopheryl acetate, phenoxyethanol, cetyl alcohol, xantham gum, polyethylene glycol (PEG), sodium cetearyl sulphate, glycerol stearate, and parfum.

The ultraviolet absorber and protectant composition may be formulated as a coating for materials and/or admixed into materials such as paint, varnish or resin. The coating may include, but is not limited to, a paint, varnish or resin.

There is further provided for any one of the first to eighth aspects of this disclosure substantially as herein described, illustrated and/or exemplified with reference to any one of the examples and/or figures herein.

BRIEF DESCRIPTION OF DRAWINGS

FIG. 1 shows reagents and conditions: (a) n-BuLi. THF, −78° C. to rt, 2-24 h, 3a-c 10-47%; (b) Pd/C, $H_2$, MeOH, EtOAc, rt, 24 h, 4a-c, 84-99%; (c) For 4a: $AlCl_3$, pyridine, PhMe, reflux, 4d, 58%; For 4b: $BCl_3$, $CH_2Cl_2$, −78° C. to rt, 4 d, 69%.

FIG. 2 shows reagents and conditions: a) PhCOCl, DMAP, $Et_3N_3$, 2-Me-THF, 0° C. to rt, 2 h, 95%; b) $AlCl_3$, PhCl, Mw (160° C., 150 W, 30 min), 78%; c) [Ru(p-cymene)$Cl_2]_2$ (2.5 mol %), $K_2S_2O_8$, TFA/TFAA, 80° C., 14 h, 72%.

FIG. 3 shows reagents and conditions: (a) $CH_3COCl$, DMAP, $Et_3N$, 2-Me-THF, 0° C. to rt, 2 h, 93%; (b) $AlCl_3$, PhCl, Mw (160° C., 150 W, 30 min), quant. (c) (i) NaOH, PhCHO, MeOH, 3 h, 67% (ii) 0.5N aq. NaOH, $H_2O_2$, rt, 4 h, 88%.

FIG. 4 shows reagents and conditions: (a) 2-Flourobenzoyl chloride, DMAP. $Et_3N$, 2-Me-THF, 0° C. to rt, 2 h, quant.; (b) $AlCl_3$, PhCl, Mw (160° C., 150 W), 30 min, 84%; (c) $K_2CO_3$, $Me_2CO$, reflux, 6 h, 86%; (d) [Ru(p-cymene)$Cl_2]_2$ (2.5 mol %), $K_2S_2O_8$, TFA/TFAA, 80° C., 12 h, 71%; (e) [Ru(p-cymene)$Cl_2]_2$ (2.5 mol %). $K_2S_2O_8$, TFA/TFAA, 80° C., 12 h, 64%.

FIG. 5 shows reagents and conditions: (a) $SnCl_4$, $Bu_3N$, $(CH_2O)_n$, PhMe, 100° C., 18 h, 77%; (b) $LiAlH_4$, THF, rt, 6 h, 81%; Benzamidine hydrochloride. $Cu(OAc)_2$. $Na_2CO_3$, PhMe, 110° C., 12 h, 62%.

FIG. 6 shows reagents and conditions: (a) $NH_2OH·HCl$, $Fe_3Cl_3$, DMF, reflux, 18 h, 80%; (b) Mw: 220° C. 200 W, 1.5 h, neat, 73%.

FIG. 7 shows reagents and conditions: (a) $Et_2O$, MeOH, rt, 18 h, 82%; (b) $PhI(OAc)_2$, $Me_2CO$, rt, 5 h, 47%.

FIG. 8 shows UV absorbance profiles of benzophenones 4c, 5 and 6 derived from anacardic acid.

FIG. 9 shows UV absorbance profiles of benzophenones 4c, 5 and 6 derived from cardanol.

FIG. 10 shows UV profiles of chalcone 13a, flavone 13b and xanthone 14.

FIG. 11 shows UV profiles of triazines 20 and 21.

FIG. 12 shows UV profiles of oxadiazole 23.

DETAILED DESCRIPTION

The general provisions of the Summary are repeated herein by way of reference thereto and are not necessarily repeated in full to avoid repetition. The detailed description and examples herein below will include particular embodiments of this disclosure and should not be considered as limiting in any way. Several alternatives may be envisioned by a person skilled in the art which does not depart from the scope of this disclosure.

As discussed herein above, cashew nut shell liquid (CNSL) has been identified as a sustainably produced biomass and chemical feedstock.

The primary phenolic constituents of CNSL include, but are not limited to, anacardic acid, cardol and cardanol. These phenolics were extracted by known organic separation means and isolated for further downstream functionalization and/or transformation and/or synthetic procedures in order to manufacture ultraviolet (UV) radiation absorbing compounds described herein. Specifically, the isolated phenolics were utilized in order to manufacture compounds having excited state intramolecular proton transfer (ESIPT) character. Said compounds having ESIPT character are for use in the prevention and/or treatment of sunburn.

Said compounds having ESIPT character may also be formulated into compositions such as coatings, paints, resins, polymers, and/or varnish and/or for use in industrial applications to treat and/or protect materials and/or buildings from exposure UV radiation. This further extension of this disclosure will ameliorate the damaging effects of UV rays responsible for the discoloration of dyes and pigments; weathering; yellowing of plastics; loss of gloss and mechanical cracking of materials (such as plastics materials).

Ideal organic UV filters display a high UV absorption in the in the region ranging from 315-400 nm (UVA) and 280-315 nm (UVB).

Typically, compounds display ESIPT character when such compound includes an intramolecular hydrogen bond (H-bond) between proton donor (—OH and —NH$_2$) and proton acceptor (=N— and —C=O) groups in close proximity to each other in a molecule.

Without being limited to theory, it is postulated that said compounds that display ESIPT character dissipate UV radiation through an efficient radiationless deactivation process by means of rapid tautomerization which proceeds via the excited-state intramolecular proton transfer (ESIPT) mechanism. This is in contrast to conventional chemical UV absorbers where radiation related decomposition can lead to unwanted side effects and unwanted by-products of decomposition that may be dangerous to human and animal health.

Apart from their petrochemical origin, another major drawback of current chemical UV absorbers is their negative effect on aquatic ecosystems due to among others, their poor biodegradability. As a result, there is a steadily growing attention from regulatory bodies and stricter regulations are being enforced. To this end, there is a need to develop new, efficient, less toxic, and eco-friendly UV filters, ideally in a sustainable fashion. More importantly, broad spectrum of UV filters capable of absorbing both UVA and UVB are required. Recently, concerns have been expressed about the carcinogenic impact of titanium dioxide requiring more research into healthier UV protectant means.

Many chemical absorbers only absorb UV radiation in one of the regions UVA, UVB or UVC. This requires several compounds to be formulated into a mixture or composition to ensure a commercial sunscreen provides adequate protection against UVA, UVB and/or UVC radiation.

In accordance with a first aspect of this disclosure there is provided a compound having excited state intramolecular proton transfer (ESIPT) character, said compound being at least one of compounds (i) to (vii) herein above.

A second aspect of this disclosure extends to one or more of the compounds (i)-(vii) for use in the treatment and/or prevention of sunburn in a human or animal body.

The compounds (i) to (vii) may be optionally substituted. One or more substituent R groups may be located at an ortho, meta and/or para position on an aromatic ring, typically a benzene ring. The ring may include more than one substituent R groups which may be the identical, or alternatively, may differ in chemical structure. The compounds (i) to (vii) may be optionally substituted with multiple R groups wherein the same R group or different R groups are linked or bonded forming chains or rings. Rings such as, but not limited to, tetrahydronaphthalenyl groups may be formed.

For compounds (i) to (vii) the groups R and/or $R_1$ and/or $R_2$ may each be at least one substituent or moiety located at an ortho, meta and/or para position on the benzene ring and may be selected from the group including: hydrogen, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, thioalkyl, arylthio, cyano, halogen, thiocarbonyl, O-carbamyl, N-carbamyl. O-thiocarbamyl, N-thiocarbamyl, C-amido, N-amido, S-sulfonamido. N-sulfonamido, C-carboxy, protected C-carboxy, O-carboxy, isocyanato, thiocyanato, isothiocyanato, nitro, nitrile, silyl, sulfenyl, sulfinyl, sulfonyl, haloalkyl, polyhaloalkyl, haloalkoxy, trihalomethanesulfonyl, trihalomethanesulfonamido, an amino, a mono-substituted amino and a di-substituted amino group, esters, alcohol, acetates and protected derivatives of any one of the aforementioned.

The compounds may be formulated into compositions for use in the treatment and/or prevention of sunburn in the human or animal body, wherein the compositions may include at least one of, but not limited to, the following group: aqua, glycerine, trisodium ethylene diamine tetraacetic acid (EDTA), tocopheryl acetate, phenoxyethanol, cetyl alcohol, xantham gum, polyethylene glycol (PEG), sodium cetearyl sulphate, glycerol stearate, and parfum.

A third aspect of this disclosure extends to use of any one or more of the compounds (i) to (vii), as per the second aspect of this disclosure, in the manufacture of a medicament for the treatment and/or prevention of sunburn in a human or animal body.

A fourth aspect of this disclosure extends to a compound having excited state intramolecular proton transfer (ESIPT) character produced from cashew nut shell liquid (CNSL), as per the second aspect of this disclosure, for use in the treatment and/or prevention of sunburn in a human or animal body. The compounds include any one or more of compounds (i) to (vii) according to the second aspect.

A fifth aspect of this disclosure extends to use of cashew nut shell liquid (CNSL) for manufacturing any one of compounds (i) to (vii) having excited state intramolecular proton transfer (ESIPT) character, wherein said compound is for the treatment and/or prevention of sunburn in a human or animal body, wherein the compounds are as per the second aspect.

A sixth aspect of this disclosure extends to a method of manufacturing a compound having excited state intramolecular proton transfer (ESIPT) character, said method comprising the following steps:
  (a). isolating phenolic compounds from cashew nut shell liquid (CNSL), preferably said phenolic compounds including at least one of but not limited to the following group: anacardic acid, cardol and cardanol;
  (b). transforming said isolated phenolic compound into any one or more of the compounds according to the second aspect of this disclosure.

The method may include one or more steps as described and/or exemplified herein below.

A seventh aspect of this disclosure extends to a compound having excited state intramolecular proton transfer (ESIPT) character manufactured in accordance with the method described and/or illustrated and/or exemplified herein.

An eighth aspect of this disclosure there is provided a method of treating and/or preventing sunburn comprising application of a compound having excited state intramolecular proton transfer (ESIPT) character produced from cashew nut shell liquid (CNSL) onto a human or animal body. Typically, the compounds include any one or more of compounds (i) to (vii) as per the second aspect, and said compounds are typically formulated into compositions for readily application onto skin of a human or animal body. The compositions generally include aerosols or creams/lotions.

Finally, a ninth aspect of this disclosure extends an ultraviolet absorber and protectant composition comprising a compound having excited state intramolecular proton transfer (ESIPT) character produced from cashew nut shell liquid (CNSL). The ultraviolet absorber composition includes at least one of the compounds (i) to (vii) according to the first or second aspects.

The ultraviolet absorber and protectant composition is formulated as a sunscreen and may include at least one of, but not limited to, the following group: aqua, glycerine, trisodium ethylene diamine tetra-acetic acid (EDTA), tocopheryl acetate, phenoxyethanol, cetyl alcohol, xantham gum, polyethylene glycol (PEG), sodium cetearyl sulphate, glycerol stearate, and parfum.

The ultraviolet absorber and protectant composition may be formulated as a coating for materials and/or admixed into materials such as paint, varnish or resin. The coating may include, but is not limited to, a paint, varnish or resin. When formulated as a coating for materials the ultraviolet absorber composition in use protects the coated material from UV radiation. This is an important application in buildings, outdoor furniture, roofs, window frames, and the like.

The Applicant surprisingly found that the compounds (i) to (vii) were UVA and UVB absorbers that did not show radiation related deactivation. The compounds did not undergo any cis-trans and/or E-Z isomerization nor decompose into harmful substituents. Surprisingly, the Applicant has found that compounds (i) to (vii) dissipate UV radiation through an efficient radiationless deactivation process by means of rapid tautomerization which proceeds via the excited-state intramolecular proton transfer (ESIPT) mechanism. Compounds (i) to (vii) for use in the treatment and/or prevention of sunburn surprisingly ameliorates at least some of the disadvantages known from the prior art.

It is also important to provide water resistant sunscreens. In the compounds (i) to (vii) according to both first and second aspects, the long alkyl chains together with the functionalization providing the ESIPT character together surprisingly provide water resistance by ensuring absorption into the skin. Known chemical sunscreens such as oxybenzone is known to readily wash off from skin, and is known to be extremely toxic to coral. This alarming finding has caused certain jurisdictions to ban oxybenzone containing sunscreens altogether. The alkyl chains may be from about 1 to about 20 carbons.

The Applicant believes that the subject matter of the disclosure described herein at least ameliorates one of the disadvantages known in the current state of the art.

Whenever a compound described herein, typically compounds (i) to (vii) of either or both of the first and second aspect of the invention is described as being "optionally substituted" that compound may be unsubstituted or substituted with one or more of the indicated substituent R groups. Likewise, when a compound is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from hydrogen, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, thioalkyl, arylthio, cyano, halogen, thiocarbonyl, O-carbamyl, N-carbamyl. O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, nitrile, silyl, sulfenyl, sulfinyl, sulfonyl, haloalkyl, polyhaloalkyl, haloalkoxy, trihalomethanesulfonyl, trihalomethanesulfonamido, an amino, a monosubstituted amino and a di-substituted amino group, esters, alcohol, acetates and protected derivatives of any one of the aforementioned.

The term "alkyl" as used herein is a broad term, and is to be given its ordinary and customary meaning to a person of ordinary skill in the art (and is not to be limited to a special or customized meaning), and refers without limitation to a straight chain or branched, acyclic or cyclic, unsaturated or saturated aliphatic hydrocarbon containing 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more carbon atoms, Representative saturated straight chain alkyls include methyl, ethyl, n-propyl, n-butyl, n-pentyl, n-hexyl, and the like; while saturated branched alkyls include isopropyl, see-butyl, isobutyl, tert-butyl, isopentyl, and the like. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Typical alkyl groups include, but are in no way limited to, methyl, ethyl, propyl, isopropyl, butyl, isobutyl, tertiary butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontanyl, and hexatriacontanoic. The alkyl group may be substituted or unsubstituted.

The term "alkoxy" as used herein is a broad term, and is to be given its ordinary and customary meaning to a person of ordinary skill in the art (and is not to be limited to a special or customized meaning), and refers without limitation to an alkyl moiety attached through an oxygen bridge (i.e., —O-alkyl) such as methoxy, ethoxy, and the like.

The term "thioalkyl" as used herein is a broad term, and is to be given its ordinary and customary meaning to a person of ordinary skill in the art (and is not to be limited to a special or customized meaning), and refers without limitation to an alkyl moiety attached through a sulfur bridge (i.e., —S-alkyl) such as methylthio, ethylthio, and the like.

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "ester" as used herein is a broad term, and is to be given its ordinary and customary meaning to a person of ordinary skill in the art (and is not to be limited to a special or customized meaning), and refers without limitation to any compound as described herein incorporating one or more ester groups, e.g., monoester, diester, triester, or polyester, or being substituted by or functionalized to include one or more ester groups. Esters include but are not limited to fatty acid esters.

The term "acetates" as used herein is a broad term, and is to be given its ordinary and customary meaning to a person of ordinary skill in the art (and is not to be limited to a special or customized meaning), and refers without limitation to any compound as described herein incorporating one or more acetate groups, such as salts, esters or other compounds incorporating a $CH_3COO—$ moiety.

SPECIFIC EMBODIMENTS OF THE DISCLOSURE

Using CNSL derived cardanol and anacardic acid as starting materials, different classes of potential UV absorbers were prepared in short and efficient synthetic sequences. Hydrogen-bonding of the phenolic hydroxyl group to a C=X-moiety of the chromophore was a central design feature to ensure an efficient ESIPT which increases photostability and reduces phototoxicity (where X is a halogen). First, benzophenones and xanthones with a neighbouring OH-group were synthesized.

SYNTHESIS

Synthesis of Benzophenones (Compounds 4c, 5 and 6)

Referring to FIG. 1, starting from CNSL derived anacardic acid, the benzyl protected methyl ester 1 was prepared using known procedures. Exposure of substituted bromo benzenes 2 (a, b, c) to n-BuLi followed by the addition of the ester 1 as shown in FIG. 1 led to the formation of protected benzophenones 3 (a,b,c). O-Debenzylation of 3 (a,b,c) using Pd/C under a hydrogen atmosphere furnished benzophenones 4 (a,b,c) in excellent yields. Benzophenone 4c contained two hydrogen-bonded phenols. Exposure of 4a to $AlCl_3$ produced compound 5, while hydrogen-bonded 2,2'-dihydroxybenzophenones 6 was obtained by treatment of 4b with $BCl_3$. FIG. 1 shows reagents and conditions: (a) n-BuLi. THF, −78° C. to rt, 2-24 h, 3a-c 10-47%; (b) Pd/C, $H_2$, MeOH, EtOAc, rt, 24 h, 4a-c, 84-99%; (c) For 4a: $AlCl_3$, pyridine, PhMe, reflux, 4d, 58%; For 4b; $BCl_3$, $CH_2Cl_2$, −78° C. to rt, 4 d, 69%.

One further benzophenone possessing two hydrogen bonded phenols was synthesized utilising the CNSL derived cardanol 7 as a starting material. Esterification of cardanol 7 with benzoyl chloride gave the ester 8 in excellent yields. This was followed by a microwave-promoted Fries rearrangement of 8 in the presence of $AlCl_3$ to furnish benzophenone 9. A palladium-mediated C—H oxygenation of 9 gave the 2,2'-dihydroxybenzophenone 11 in 61% yield (FIG. 2). FIG. 2 shows reagents and conditions: a) PhCOCl, DMAP, $Et_3N$, 2-Me-THF, 0° C. to rt, 2 h, 95%; b) $AlCl_3$, PhCl, Mw (160° C., 150 W, 30 min), 78%; c), [Ru(p-cymene)$Cl_2]_2$ (2.5 mol %), $K_2S_2O_8$, TFA/TFAA, 80° C., 14 h, 72%.

Synthesis of 3-Hydroxyflavone (Compound Number 13)

Another class of potential UV absorbers possessing a hydrogen bonded hydroxyl group to a carbonyl substituent are the flavones. Utilizing CNSL derived cardanol 7 the first step was accomplished in a similar manner to FIG. 2 by initial O-acetylation of cardanol 7 to furnish 11. Again, a microwave assisted Fries rearrangement of 11 under $AlCl_3$ catalysis afforded the 1-(2-hydroxyphenyl)ethanone 12 in an excellent overall yield. Aldol condensation of 12 with benzaldehyde, afforded the aldol intermediate 13a. If this was followed by in-situ oxidation with hydrogen peroxide it gave the desired 3-hydroxyflavone 13b, in a reasonable yield of 67% over the two steps, as shown in FIG. 3. Since acetic acid and benzaldehyde are derived from wood based chemicals, in other words xylochemicals, the entire molecular skeleton of 13a and 13b is derived from biomass. FIG. 3 shows reagents and conditions: (a) $CH_3COCl$, DMAP, $Et_3N$, 2-Me-THF, 0° C. to rt, 2 h, 93%; (b) $AlCh_3$, PhCl, Mw (160° C., 150 W, 30 min), quant. (c) (i) NaOH, PhCHO, MeOH, 3 h, 67% (ii) 0.5N aq. NaOH, $H_2O_2$, rt, 4 h, 88%. Since acetic acid and benzaldehyde are xylochemicals, the entire molecular skeletons of 13a and 13b are derived from biomass.

Synthesis of Xanthone Derivative (Compound Number 14)

The next class of compounds investigated as potential UV-absorbers were hydrogen-bonded xanthones. As an example, the 1,8-dihydroxyxathone 14 was synthesized from cardanol from CNSL. Using the methodology previously described, the Fries rearrangement of 15 was used to assemble benzophenone 16 (FIG. 4) in 84% over the two steps. Refluxing of 16 with potassium carbonate in acetone yielded the xanthone 17. A ruthenium catalysed C—H oxygenation of 16 furnished the desired 1,8-dihydroxyxathone 14 over two steps in a mediocre yield of 54%. Since 2-fluorobenzoic acid can be synthesised from anthranilic acid, the entire molecular skeleton of 14 is derived by means of a xylochemical synthesis. FIG. 4 shows reagents and conditions: (a) 2-Flourobenzoyl chloride. DMAP, $Et_3N$, 2-Me-THF, 0° C. to t, 2 h. quant.; (b) $AlCl_3$, PhCl, Mw (160° C., 150 W), 30 min, 84%; (c) $K_2CO_3$, $Me_2CO$, reflux, 6 h, 86%; (d) [Ru(p-cymene)$Cl_2]_2$ (2.5 mol %), $K_2S_2O_8$, TFA/TFAA, 80° C., 12 h, 71%; (e) [Ru(p-cymene)$Cl_2]_2$ (2.5 mol %), $K_2S_2O_8$, TFA/TFAA, 80° C., 12 h, 64%.

Synthesis of Triazines (Compound Numbers 20 and 21)

Nitrogen containing compounds such as 2-hydroxytriazines were investigated. 2-(4,6-diphenyl-1,3,5-triazin-2-yl) phenol 20 was synthesized from CNSL derived cardanol in three steps. The $SnCl_4$-mediated formylation of cardanol 7 gave benzaldehyde 18 in an excellent yield, which was followed by $LiAlH_4$-reduction of the aldehyde 18 to afford benzyl alcohol 19, as shown in FIG. 5. Exposure of the alcohol 19 to benzamidine under $Cu(OAc)_2$ catalysis afforded the 2-(4,6-diphenyl-1,3,5-triazin-2-yl)phenol 20 in a 62% yield. The second organic building block, benzamidine can be prepared from benzoic acid or benzaldehyde and thus can be regarded as compatible with xylochemical principles. FIG. 5 shows reagents and conditions: (a) $SnCl_4$, $Bu_3N$, $(CH_2O)_n$, PhMe, 100° C., 18 h, 77%; (b) $LiAlH_4$, THF, rt, 6 h, 81%; Benzamidine hydrochloride, $Cu(OAc)_2$, $Na_2CO_3$, PhMe, 110° C., 12 h, 62%.

In order to assess the effect of increasing the number of intramolecular hydrogen bonded N—H units on IV absorbance, 2,2',2"-(1,3,5-triazine-2,4,6-triyl)triphenol 22 was also prepared. It was envisioned that this could easily be prepared from the formylated cardanol intermediate 18 as shown in FIG. 6. Reacting aldehyde 18 with hydroxylamine hydrochloride and FeCl$_3$ in DMF under reflux conditions yielded nitrile 22 which could be trimerized through microwave irradiation to furnish s-triazine 21 in 73% yield, thus furnishing a triazine with three potential hydrogen bonded N—H substituents. FIG. 6 shows reagents and conditions: (a) NH$_2$OH·HCl, FeCl$_3$, DMF, reflux, 18 h, 80%; (b) Mw: 220° C., 200 W, 1.5 h, neat, 73%.

Synthesis of Oxadiazole (Compound Number 23)

Oxadiazole 23 was synthesized which should also display N—H hydrogen bonding and hence be a possible UV filter was the oxadiazole 23. Exposure of the aldehyde 18 to the hydrazide of veratric acid 24 afforded 25. Condensation and oxidative oxadiazole ring formation yielded 23 in an overall yield of 39% over two steps (FIG. 7). Figure shows reagents and conditions: (a) Et$_2$O, MeOH, rt, 18 h, 82%; (b) PhI (OAc)$_2$, Me$_2$CO, rt, 5 h, 47%.

UV Absorbance Profiles of the Synthesized Compounds

The synthesized compounds 4c, 5, 6, 9, 10, 13a, 13b, 14, 20, 21, and 23, were analysed for their UV absorbances and their molar absorptivity coefficients (e) were determined. Analysis of UV absorbance was done in order to establish whether the compounds exhibited e values in the UV-B and UV-A regions of the UV spectra commensurate with those for UV absorbers.

The 2,2'-dihydroxybenzophenone 4c synthesized from anacardic acid showed reasonable UV absorbance in the UVA region with the experimental F values of 10,538 L mol$^{-1}$ cm$^{-1}$ at 335 nm and a high absorbance of 36,366 L mol$^{-1}$ cm$^{-1}$ at 261 nm albeit outside both UVA and UVB region (FIG. 8). The benzophenone 5 exhibited ε values of 8,785 L mol$^{-1}$ cm$^{-1}$ at 374 nm and 18,439 L mol$^{-1}$ cm$^{-1}$ at 265 nm. Benzophenone 6 showed excellent UVA absorbance with ε values 25,014 L mol$^{-1}$ cm$^{-1}$ at 358 nm and 34,096 L mol$^{-1}$ cm$^{-1}$ at 287 nm.

FIG. 8 shows UV absorbance profiles of benzophenones 4c, 5 and 6 derived from anacardic acid. In comparison, the benzophenones 9 and 10 derived from cardanol showed excellent absorption at the edge of the UVB region with experimental ε values of 47,909 L mol$^{-1}$ cm$^{-1}$ and 31.659 L mol$^{-1}$ cm$^{-1}$ at 279 nm and 282 nm for mono- and dihydroxy-benzophenones respectively as shown in FIG. 9. FIG. 9 shows UV absorbance profiles of benzophenones 4c, 5 and 6 derived from cardanol. 3-Hydroxyflavone 13b displayed an excellent absorption profile in the UVA region with experimental ε values of 39.870 L mol$^{-1}$ cm$^{-1}$ at 314 nm and 44.979 L mol$^{-1}$ cm$^{-1}$ at 345 nm as shown in FIG. 3. The intermediate phenylpropanone 13a showed an experimental e value of 20,403 L mol$^{-1}$ cm$^{-1}$ at 314 nm and 10, 250 L mol$^{-1}$ cm$^{-1}$ at 347 nm. Dihydroxy xanthone 14 exhibited a good UV absorption profile with ε value of 23.765 L mol$^{-1}$ cm$^{-1}$ at 254 nm (FIG. 10) However, UVC is less relevant at sea level due to the filtering function of the atmospheric ozone layer. FIG. 10 shows UV profiles of chalcone 13a, flavone 13b and xanthone 14.

The s-triazine 21 showed the best UV absorbance in both the UVA and UVB region with experimental ε value of 21,452 L mol$^{-1}$ cm$^{-1}$ at 300 nm and 12.515 L mol$^{-1}$ cm$^{-1}$ at 364 nm. These results suggest 21 to be classified as a broad spectrum UV filtering agent as it showed excellent results in both relevant UV regions. The 2-(4,6-diphenyl-1,3,5-triazin-2-yl)phenol 20 on the other hand exhibited excellent UV absorbance at the beginning of the UVB region with an ε value of 29,252 L mol$^{-1}$ cm$^{-1}$ at 278 nm (FIG. 11). FIG. 11 shows UV profiles of triazines 20 and 21.

The oxadiazole 23 displayed moderate UV absorbance in the UVA region with experimental ε values of 6,367 L mol$^{-1}$ cm$^{-1}$ at 326 nm and 3,373 L mol$^{-1}$ cm$^{-1}$ at 293 nm as shown in FIG. 12. FIG. 12 shows UV profiles of oxadiazole 23.

Prior Art Chemical Absorbers:

Commercially available sunscreen protectants oxybenzone (OB), 2-ethylhexyl 4-methoxycinnamate (OMC) and avobenzone) were reported to show experimental molar absorption coefficients of 15,150 at 287 nm, 39,470 at 356 nm and 31,670 at 310 nm respectively. Some of our compounds are in the same ball park range of absorption and others are even superior to the commercial ones.

Conclusions

Various classes of UV filters were synthesized using CNSL as a non-edible bio-renewable chemical feedstock. In addition, where possible, the principles of xylochemistry were utilized. The UV profiles of these compounds are promising for a potential application as sunscreens agents, in paints and other related industries. Cytotoxicity evaluations of these compounds are currently being undertaken. Without being limited to theory, it is postulated that the long aliphatic chain improves the lipophilicity of the manufactured compound allowing the compound(s) to be applied to human or animal skin with greater ease and prevent the compound being washed off with water, therein providing for a good sunscreen product when in use. The aliphatic chains may be from about 1 to about 20 carbons, but typically exemplified herein as 14 carbons.

FURTHER DETAILED SYNTHETIC PROTOCOLS

Solvents used for chromatographic techniques (ethyl acetate, cyclohexane and n-hexane) were distilled prior to use by means of conventional distillation processes. The solvents employed in reactions were first dried over a suitable drying agent, followed by distillation under an inert atmosphere (argon or nitrogen gas). Acetonitrile and dichloromethane were distilled over calcium hydride, whereas tetrahydrofuran was distilled over sodium with benzophenone as an indicator. Toluene was distilled over sodium. All the required chemicals or reagents were obtained from TCI, Acros Organics, Fluka. Sigma Aldrich or Merck and were used without further purification.

Normal chromatography was performed on silica gel 60 (Macherey-Nagel, particle size 0.063-0.200 mm), employing both isocratic and gradient eluent systems. Flash-chromatographic purifications were performed on silica gel (Acros Organics, particle size 35-70 μm) using either a semiautomatic Biotage Isolera One system with an integrated UV detector and silica cartridges or hand-packed columns with nitrogen pressure of 0.4-0.6 bar. Thin layer chromatography (TLC) of the compounds was executed either on Macherey-Nagel Alugram Silica G/UV254 plates pre-coated with 0.25 mm silica gel 60 or on Merck TLC Silica 60 F$_{254}$ plates. The TLC plates were viewed under UV light (254 nm and 366 nm). Nuclear magnetic resonance (NMR) spectra were recorded on either a Bruker AVANCE, a Bruker AVANCE III HD (both 300 MHz), a Bruker AVANCE II (400 MHz), a Bruker AVANCE III 500 MHz or a Bruker AVANCE III (600 MHz) spectrometer. All chemical shift values (δ) are reported in parts per million relative to tetramethylsilane (TMS) referenced against TMS ($\delta_{TMS}$=0 ppm) or against the signal of residual protonated solvent (CDCl$_3$: $\delta_{1H}$=7.26 ppm, $\delta_{13C}$=77.16 ppm; DMSO-d$_6$: $\delta_{1H}$=2.50 ppm, $\delta_{13C}$=39.52 ppm respectively). Coupling constants (J-values) are given in Hertz (Hz). The infrared spectra were recorded on a Bruker Tensor 27 FT-IR spectrometer with a diamond ATR unit. The measurements are reported on the wavenumber scale ($\tilde{v}$, [cm$^{-1}$]).

Melting points were determined on a Reichert hot-stage microscope or on a Krüss-Optronic KSP 1N apparatus, and remain uncorrected. All crystalline compounds were recrystallized in the appropriate solvents prior to melting point determination. Microwave reactions were conducted in a CEM Discover microwave.

High resolution mass spectra (HRMS) were obtained with a Waters-LCT-Premier mass spectrometer. The sample was dissolved in methanol to a concentration of 2 ng/μl and introduced by direct infusion. The ionization mode was electrospray (ESI) positive with a capillary voltage of 2500 V and a desolvation temperature of 250° C. using nitrogen gas at 250 L/hr. Alternatively, an Agilent 6545 QTOF-MS with a suitable external calibrant was used for ESI-HRMS.

Methyl 2-benzyloxy-6-pentadecylbenzoate 1

A suspension of calcium anacardate (20.0 g, ca. 52.3 mmol) in aqueous HCl (10%, 100 mL) was stirred for 3 h at rt. Afterwards, EtOAc (100 mL) was added and the mixture was stirred for 1 h and the layers were separated. The aqueous layer was extracted with EtOAc (2×50 mL) and the combined organic extracts were washed with brine (30 mL). After drying over MgSO$_4$ and evaporation of the solvent the anacardic acids were obtained as a brown oil (13.7 g, ca. 39.9 mmol, 76%). IR (Q/cm$^{-1}$): 2923, 2853, 1644, 1607, 1447, 1245, 1207, 1166, 910, 822, 783; $^1$H NMR (300 MHz, Chloroform-d) δ 11.01 (s, 1H), 9.62 (s, 2H), 7.35 (dd, J=8.3, 7.5 Hz, 1H), 6.86 (dd, J=8.4, 1.2 Hz, 1H), 6.76 (dd, J=7.5, 1.2 Hz, 1H), 5.81 (ddt, J=17.3, 10.1, 6.2 Hz, 0.4H), 5.51-5.24 (m, 4H), 5.04 (dq, J=17.1, 1.8 Hz, 0.4H), 4.97 (dq, J=10.1, 1.6 Hz, 0.4H), 3.05-2.94 (m, 2H), 2.87-2.68 (m, 2H), 2.04-1.94 (m, 3H), 1.69-1.53 (m, 2H), 1.44-1.19 (m, 21H), 0.99-4.83 (m, 3H) ppm; $^{13}$C NMR (76 MHz, Chloroform-d) δ 176.0, 163.5, 147.7, 136.8, 135.3, 130.4, 130.1, 129.9, 129.8, 129.3, 128.1, 128.0, 127.6, 126.8, 122.7, 115.8, 114.7, 110.5, 36.4, 32.0, 31.8, 31.5, 29.7, 29.4, 29.23, 29.0, 27.2, 25.6, 22.8, 22.6, 14.1; MS (ESI+): m/z (%)=343.5 (100) [M$_{3DB}$+H]$^+$, 345.5 (97) [M$_{2DB}$+H]$^+$, 347.4 (100) [M$_{1DB}$+H]$^+$, 365.5 (26) [M$_{3DB}$+Na]$^+$, 367.4 (35) [M$_{2DB}$+Na]$^+$, 369.4 (39) [M$_{1DB}$+Na]$^+$. The index "DB" denotes the number of double bonds present. The analytical data are in accordance with the literature. [20]

Palladium on activated charcoal (10 wt %, 600 mg, 0.56 mmol) was added to a solution of anacardic acids (10.2 g, 29.6 mmol) in MeOH (125 mL) under an atmosphere of nitrogen. The flask was purged with hydrogen and the suspension was stirred for 60 h at rt under an atmosphere of hydrogen. Afterwards, the flask was purged with nitrogen and the reaction mixture was filtered through Celite®. After rinsing with MeOH (300 mL), the solvent was evaporated and 2-hydroxy-6-pentadecylbenzoic acid was obtained as a brownish solid (10.0 g, 28.8 mmol, 97%). Mp. 87-88° C.; IR ($\tilde{v}$/cm$^{-1}$): 2916, 2850, 1651, 1604, 1445, 1248, 1218, 815, 724, 707; $^1$H NMR (300 MHz, Chloroform-d) δ 7.36 (t, J=7.9 Hz, 1H, H4), 6.87 (d, J=8.3 Hz, 1H, H3), 6.77 (dd, J=7.5, 1.2 Hz, 1H, H5), 2.98 (dd, J=9.1, 6.4 Hz, 2H, H1'), 1.65-1.55 (m, 2H, H2'), 1.39-1.25 (m, 24H, H3'-H14'), 0.88 (t, J=6.3 Hz, 3H, H15') ppm; $^{13}$C NMR (76 MHz, Chloroform-d) δ 176.0 (CO$_2$), 163.6 (C2), 147.8 (C6), 135.4 (C4), 122.7 (C5), 115.8 (C3), 110.4 (C1), 36.5 (C1'), 32.0 (C13'), 31.9 (C2'), 29.8, 29.7 (6C), 29.6, 29.5, 29.4, 22.7 (C14'), 14.1 (C15') ppm; MS (ESI-): m/z (%)=347.3 (100) [M-H]$^-$, 717.6 (12) [2M+Na-2H]$^-$; HRMS (ESI-). Found (M-H)$^-$ 347.2592, C$_{22}$H$_{35}$O$_3$(M-H)$^-$ requires 347.2592. The analytical data are in accordance with the literature. [20]

Conc. sulfuric acid (2.50 mL, 139 μmol) was carefully added to a stirred solution of 2-hydroxy-6-pentadecylbenzoic acid (2.00 g, 5.74 mmol) in MeOH (50 mL). The resulting mixture was stirred at reflux overnight and then cooled to rt. The solvent was evaporated and an aqueous saturated NaHCO$_3$ solution (30 mL) was added to the residue. After extraction with EtOAc (3×25 mL), the combined organic extracts were subsequently washed with water and brine (20 mL each) and dried over MgSO$_4$. The solvent was evaporated and the crude product was purified by column chromatography on silica gel (20% EtOAc/hexane) affording methyl 2-hydroxy-6-pentadecylbenzoate as a pale brown solid (1.67 g, 4.71 mmol, 82%). Mp. 41.5-43° C.; IR ($\tilde{v}$/cm$^{-1}$): 2914, 2850, 1662, 1578, 1441, 1315, 1201, 1120, 946, 817, 742; $^1$H NMR (300 MHz, Chloroform-d) δ 11.10 (s, 1H, OH), 7.28 (dd, $^3$J$_{4,3}$=8.4 Hz, $^3$J$_{4,5}$=7.5 Hz, 1H, H4), 6.83 (dd, J=7.5, 1.3 Hz, 1H, H3), 6.71 (dd, J=7.5, 1.3 Hz, 1H, H5), 3.95 (s, 3H, CO$_2$CH$_3$), 2.88 (dd, J=8.8, 6.8 Hz, 2H, H1'), 1.56-1.47 (m, 2H, H2'), 1.36-1.24 (m, 24H, H3'-H14'), 0.88 (t, J=7.0 Hz, 3H, H15') ppm; $^{13}$C NMR (76 MHz, Chloroform-d) δ 171.9 (CO$_2$CH$_3$), 162.6 (C2), 146.2 (C6), 134.1 (C4), 122.4 (C5), 115.6 (C3) 111.8 (C1) 52.0 (CO$_2$CH$_3$), 36.6 (C1'), 32.1 (C13'), 31.9 (C2'), 29.9, 29.7-29.6 (7C), 29.5, 29.3, 22.7 (C14'), 14.1 (C15') ppm; MS (ESI-): m/z (%)=361.4 (100) [M-H]$^-$; HRMS (ESI+). Found (M+H)$^+$ 363.2889, C$_{23}$H$_{39}$O$_3$ (M+H)$^+$ requires 363.2894. The analytical data are in accordance with the literature. [21]

A suspension of methyl 2-hydroxy-6-pentadecylbenzoate (1.20 g, 3.31 mmol) and K$_2$CO$_3$ (915 mg, 6.62 mmol) in acetone (20 mL) was stirred at reflux for 10 min. After cooling to rt, benzyl bromide (591 μL, 4.97 mmol) was carefully added and the mixture was stirred for 8 h at reflux under an atmosphere of nitrogen. The mixture was cooled to rt, filtered through Celite® and rinsed with acetone (100 mL). After evaporating the solvent, the crude product was purified by column chromatography on silica gel (5% EtOAc/hexane) to obtain methyl 2-benzyloxy-6-pentadecylbenzoate 1 as a colourless solid (1.25 g, 2.76 mmol, 83%). Mp. 29-31° C.; IR ($\tilde{v}$/cm$^{-1}$): 2922, 2852, 1732, 1583, 1453, 1264, 1109, 1066, 734; $^1$H NMR (300 MHz, Chloroform-d) δ 7.42-7.29 (m, 5H, Bn-42-Bn-H6), 7.23 (dd, J=8.4, J=7.7 Hz, 1H, H4), 6.83 (d, J=7.5 Hz, 1H, H5), 6.78 (dd, J=7.7, 1.0 Hz, 1H, H3), 5.10 (s, 2H, Bn-CH$_2$), 3.89 (s, 3H, CO$_2$CH$_3$), 2.59-2.53 (m, 2H, H1'), 1.63-1.54 (m, 2, 112), 1.33-1.23 (m, 24H, H3'-H14'), 0.88 (t, J=6.5 Hz, 3H, H15') ppm; $^{13}$C NMR (76 MHz, Chloroform-d) δ 168.8 (CO$_2$CH$_3$), 155.4 (C2), 141.5 (C6), 136.9 (Bn-C1), 130.1 (C4), 128.4 (2C, Bn-C3, Bn-C5), 127.7 (Bn-C4), 126.8 (2C, Bn-C2, Bn-C6), 124.1 (C1), 121.8 (C5), 110.0 (C3), 70.4 (Bn-CH$_2$), 52.0 (CO$_2$CH$_3$), 33.5 (C1'), 31.9 (C13'), 31.1 (C2'), 29.7 (6C), 29.5 (2C), 29.4, 29.3, 22.7 (C14'), 14.1 (C15') ppm; MS (ESI+): m/z (%)=21.5 (98) [M-OMe+H]$^+$, 453.5 (100) [M+H]$^+$, 475.4 (54) [M+Na]$^+$; HRMS (ESP+). Found (M+H)$^+$ 453.3358, C$_{30}$H$_{45}$O$_3$ (M+H)$^+$ requires 453.3363.

General Procedure for the Synthesis of Benzophenones 3a-c

The respective bromobenzene 2a-c (1.05 mmol) was added to a flame dried 50 ml. Schlenk flask and the flask was subsequently evacuated and filled with nitrogen three times. Dry THF (5 mL) was added and the solution was cooled to −83° C. while stirring. A solution of n-butyl lithium in hexane (1.39 m, 752 μL, 1.05 mmol) was added during 15 min. The resulting mixture was left stirring at −83° C. for 1 h and a solution of methyl 2-benzyloxy-6-pentadecylbenzoate 1 (430 mg, 0.95 mmol) in dry THF (5 mL) was added during 15 min. After stirring for 1 h at −83° C. the solution was slowly brought to rt and stirred further. The mixture was quenched with a saturated NH₄Cl solution (10 mL) and extracted with EtOAc (3×10 mL). The combined organic extracts were dried over MgSO₄ and evaporated. The crude product was purified by column chromatography on silica gel (EtOAc/hexane).

[2-(Benzyloxy)-6-pentadecylphenyl](2,5-dimethoxyphenyl)methanone 3a

The title compound was synthesized following the general procedure from 2,5-dimethoxybromobenzene 2a (157 μL, 1.05 mmol) and methyl 2-benzyloxy-6-pentadecylbenzoate 1 (430 mg, 0.95 mmol). The resulting solution was stirred over night at rt and the crude product was purified by column chromatography on silica gel (5-10% EtOAc/hexane) to yield [2-(benzyloxy)-6-pentadecylphenyl](2,5-dimethoxyphenyl)methanone 3a as colourless solid (245 mg, 438 μmol, 46%). Mp. 53.5-54.5° C.; IR ($\tilde{v}$/cm$^{-1}$): 2923, 2853, 1656, 1579, 1495, 1464, 1281, 1221, 1048, 745; $^1$H NMR (300 MHz, Chloroform-d) δ 7.26-7.18 (m, 5H, H6, H4', Bn-H3, Bn-H4, Bn-H5), 7.04-6.97 (m, 3H, H4, Bn-H2, Bn-H6), 6.86 (d, J=7.9 Hz, 1H, H5'), 6.84 (d, J=8.9 Hz, 1H, H3), 6.75 (dd, J=8.3, 0.9 Hz, 1H, H3'), 4.91 (s, 2H, Bn-CH₂), 3.72 (s, 3H, C5-OCH₃), 3.52 (s, 3H, C2-OCH₃), 2.57-2.51 (m, 2H, H1''), 1.57-1.50 (m, 2H, H2''), 1.33-1.20 (m, 24H, H3''-H14''), 0.88 (t, J=7.0 Hz, 3H, H15'') ppm; $^{13}$C NMR (76 MHz, Chloroform-d) δ 196.5 (C=O), 155.6 (C2'), 153.8 (C2), 153.3 (C5), 141.6 (C6'), 136.8 (Bn-C1), 132.0 (C1'), 129.6 (C1), 129.4 (C4'), 128.1 (2C, Bn-C3, Bn-C5), 127.4 (Bn-C4), 126.8 (2C, Bn-C2, Bn-C6), 122.1 (C5'), 120.0 (C4), 115.2 (C6), 114.0 (C3), 109.3 (C3'), 56.4 (C2-OCH₃), 55.7 (C5-OCH₃), 33.1 (C1''), 31.9 (C13''), 31.2 (C2''), 29.7 (6C), 29.6 (2C), 29.4 (2C), 22.7 (C14''), 14.1 (C15'') ppm; MS (ESI+): m/z: (%)=559.5 (100) [M+H]⁺, 581.5 (12) [M+Na]⁺; HRMS (ESI+). Found (M+H)' 559.3776, CH₃₇H₅₁O₄(M+H)⁺ requires 559.3782.

[2-(Benzyloxy)-6-pentadecylphenyl](2,4,5-trimethoxyphenyl)methanone 3b

NBS (2.12 g, 11.9 mmol) was added to a solution of 1,2,4-trimethoxybenzene (2.00 g, 11.9 mmol) in dry CH₂Cl₂ (20 mL) under an atmosphere of nitrogen. The resulting solution was heated to reflux and stirred overnight. After cooling to rt, the solution was washed with an aqueous saturated Na₂S₂O solution (15 mL) before the aqueous layer was extracted with CH₂CL₂ (2×15 mL). The combined organic extracts were dried over MgSO₄ and evaporated. The crude product was purified by column chromatography on silica gel (10% EtOAc/hexane) to obtain 2,4,5-trimethoxybromobenzene as a colourless solid (2.61 g, 10.6 mmol, 89/6). Mp. 56-58° C.; IR ($\tilde{v}$/cm$^{-1}$):=2999, 2942, 2843, 1505, 1451, 1378, 1204, 1.166, 1022, 838, 799; $^1$H NMR (300 MHz, Chloroform-d) δ 7.02 (s, 1H H6), 6.55 (s, 1H, H3), 3.87 (s, 3H, C4-OCH₃), 3.85 (s, 3H, C2-OCH₃), 3.82 (s, 3H, C5-OCH₃) ppm; $^{13}$C NMR (76 MHz, Chloroform-d) δ 150.3 (C2), 149.2 (C4), 143.8 (C5), 116.5 (C6), 101.1 (C1), 99.0 (C3), 57.2 (C2-OCH), 56.7 (C5-OCH₃), 56.3 (C4-OCH₃) ppm; MS (ESI+): m/z: (%)=246.1 (100) [M(Br⁷⁹)+H]', 248.1 (98) [M(Br⁸¹)+H]'. The analytical data are in accordance with the literature. [22]

[2-(Benzyloxy)-6-pentadecylphenyl](2,4,5-trimethoxyphenyl)methanone 3c

The title compound was synthesized following the general procedure from 2,4,5-trimethoxybromobenzene 2b (258 mg, 1.05 mmol) and methyl 2-benzyloxy-6-pentadecylbenzoate 1 (430 mg, 0.95 mmol). The resulting solution was stirred for 1 h at rt and the crude product was purified by column chromatography on silica gel (10-50% EtOAc/hexane) to yield [2-(benzyloxy)-6-pentadecylphenyl](2,4,5-trimethoxyphenyl)methanone 3b as yellowish solid (264 mg, 448 μmol, 47%). Mp. 53.5-55° C.; IR ($\tilde{v}$/cm$^{-1}$): 2923, 2852, 1599, 1579, 1511, 1464, 1272, 1213, 1029, 739; $^1$H NMR (300 MHz, Chloroform-d) δ 7.38 (s, 1H, H6), 7.22-7.16 (m, 4H, H4', Bn-H3, Bn-H4, Bn-H5), 7.07-7.02 (m, 2H, Bn-H2, Bn-H6), 6.86 (dd, J=7.7, 0.9 Hz, 1H, H5'), 6.75 (dd, J=8.3, 0.9 Hz, 1H, H3'), 6.41 (s, 1H, H3), 4.96 (s, 2H, Bn-CH₂), 3.92 (s, 3H, C2-OCH₃/C4-OCH₃), 3.82 (s, 3H, C5-OCH₃), 3.49 (s, 3H, C2-OCH₃/C4-OCH₃), 2.55-2.48 (m, 2H, H''), 1.54-1.48 (m, 2H, H2''), 1.27-1.19 (m, 24H, H3''-H14''), 0.88 (t, J=7.0 Hz, 3H, H15'') ppm; $^{13}$C NMR (76 MHz, Chloroform-d) δ 194.4 (C=O), 156.0 (C2/C4), 155.2 (C2'), 154.1 (C2/C4), 143.1 (C5), 140.9 (C6'), 137.1 (Bn-C1), 133.1 (C1'), 128.8 (C4'), 128.1 (2C, Bn-C3, Bn-C5), 127.4 (Bn-C4), 126.7 (2C, Bn-C2, Bn-C6), 122.0 (C5'), 120.7 (C1), 113.8 (C6), 109.3 (C3'), 97.3 (C3), 70.0 (Bn-CH₂), 56.5 (C2-OCH₃/C4-OCH₃), 56.3 (C5-OCH), 56.0 (C2-OCH₃/C4-OCH₃), 33.0 (C1''), 31.9 (C13'), 31.0 (C2''), 29.7 (6C), 29.6, 29.5, 29.4, 29.3, 22.7 (C14'), 14.1 (C15'') ppm; MS (ESI+): m/z (%)=555.5 (100) [M-OMe+1H]⁺, 587.7 (29) [M+H]⁺; HRMS (ESI+): Found (M+H)⁺ 589.3882, C₃₈H₅₃O₅ (M+H)⁺ requires 589.3888.

[2-(Benzyloxy)-6-pentadecylphenyl](2-benzyloxyphenyl)methanone 3c

A suspension of 2-bromophenol (611 μL, 5.78 mmol) and K₂CO₃ (1.20 g, 8.70 mmol) in acetone (10 mL) was stirred at reflux under an atmosphere of nitrogen for 10 min. Benzyl bromide (1.03 mL, 8.70 mmol) was then added dropwise and the mixture was stirred for 3 h at reflux. After cooling to rt, CH₂Cl₂ (15 mL) was added and the mixture was washed with water and brine (15 mL each). The organic layer was dried over MgSO₄ and evaporated. The crude product was purified by column chromatography on silica gel (5% EtOAc/hexane) to obtain 2-benzyloxybromobenzene 2c as a yellowish oil (1.29 g, 4.90 mmol, 85%). IR ($\tilde{v}$/cm$^{-3}$): 3064, 2870, 1586, 1476, 1441, 1379, 1276, 1051, 1029, 742; $^1$H NMR (300 MHz, Chloroform-d) δ 7.55 (dd, J=7.9, 1.6 Hz, 11H, H6), 7.49-7.46 (m, 2H, Bn-H2, Bn-H6), 7.41-7.35 (m, 2H, Bn-H3, Bn-15), 7.34-7.31 (m, 1H, Bn-H4), 7.22 (ddd, J=8.2, 7.4, 1.6 Hz, 1H, H4), 6.92 (dd, J=8.3, 1.4 Hz, 1 Hz, H3), 6.85 (td, J=7.9, 1.4 Hz, 1H, H5), 5.15 (s, 2H, Bn-CH₂) ppm; $^{13}$C NMR (76 MHz, Chloroform-d) δ 155.0 (C2), 136.5 (Bn-C1), 133.4 (C6), 128.5 (2C, Bn-C3, Bn-C5), 128.4 (C4), 127.9 (Bn-C4), 127.0 (2C, Bn-C2, Bn-C6), 122.1 (C5), 113.9 (3), 112.5 (C1), 70.8 (Bn-CH₂) ppm; MS (ESI+): m/z (%) 277.0 (100)[M(Br⁷⁹)+NH₄]⁺, 279.0 (78) [M(Br⁸¹)+NH₄]⁺. The analytical data are in accordance with the literature. [23]

Utilizing the synthesized 2-benzyloxybromobenzene the title compound was synthesized following the general procedure from 2-benzyloxybromobenzene 2c (275 mg, 1.05 mmol) and methyl 2-benzyloxy-6-pentadecylbenzoate 1 (430 mg, 0.95 mmol). The resulting solution was stirred for 48 h at rt and the crude product was purified by column chromatography on silica gel (2.5-5% EtOAc/hexane) to yield [2-(benzyloxy)-6-pentadecylphenyl](2-benzyloxyphenyl)methanone 3c as colourless oil (57.5 mg, 94.5 μmol, 10%). IR (v/cm$^{-1}$): 2923, 2853, 1653, 1595, 1580, 1450, 1379, 1297, 1052, 925, 750; $^1$H NMR (500 MHz, Chloroform-d) δ 7.74 (d, J=7.7 Hz, 1H, H6), 7.42 (t, J=7.9 Hz, 1H, H4), 7.25-7.21 (m, 3H, Bn-H3, Bn-H5, Bn'-4), 7.17-7.13 (m, 4H, H4', Bn-4, Bn'-3, Bn'-5), 7.03-7.01 (m, 3H, H5, Bn-H2, Bn-H6), 6.98-6.93 (m, 3H, H3, Bn'-H2, Bn'-H6), 6.77 (d, J=7.9 Hz, 1H, H5'), 6.67 (d, J=7.9 Hz, 1H, H3'), 4.86 (s, 2H, Bn-CH₂), 4.84 (s, 2H, Bn'-CH₂), 2.49 (dd, J=9.2, 7.3 Hz, 2H, H1''), 1.46 (p, J=7.3 Hz, 2H, H2''), 1.28-1.16 (m, 24H, H3''-H14''), 0.88 (t, J=6.9 Hz, 3H, H15'') ppm; $^{13}$C NMR (126 MHz, Chloroform-d) δ 196.7 (C=O), 158.2 (C2), 155.6 (C2'), 141.8 (C6), 136.9 (Bn'-C1), 136.2 (Bn-C1), 133.5 (C4), 132.1 (C1'), 131.6 (C6), 129.6 (C1), 129.4 (C4'), 128.2 (2C, Bn-C3, Bn-C5), 128.1 (2C, Bn'-C3, Bn'-C5), 127.5 (Bn-C4), 127.4 (Bn'-C4), 127.1 (2C, Bn-C2, Bn-C6), 126.8 (2C, Bn'-C2, Bn'-C6), 122.2 (C5'), 120.6 (C5), 113.0 (C3), 109.4 (C3'), 70.3 (Bn-CH$_2$), 69.9 (Bn'-CH$_2$), 33.1 (C1''), 31.9 (C13''), 31.2 (C2''), 29.7 (6C), 29.6, 29.5, 29.4, 29.3, 22.7 (C14''), 14.1 (C15'') ppm; MS (ESI+): m/z (%)=605.5 (100) [M+H]$^+$, 627.5 (53) [M+Na]$^+$; HRMS (ESI+). Found (M+H)$^+$ 605.3976, C$_{42}$H$_{53}$O$_3$ (M+H)$^+$ requires 605.3989.

General Procedure for the Synthesis of Hydroxybenzophenones 4a-c

Palladium on activated charcoal (10 wt %) was added to a solution of the respective benzophenone 3a-c dissolved in a mixture of MeOH/EtOAc (10/1) under an atmosphere of nitrogen. The flask was purged with hydrogen and the suspension was stirred over night at rt. After filtration through Celite® the residue w as rinsed with MeOH and EtOAc (50 mL each) and the solvents were evaporated to afford the desired products 4a-c.

(2-Pentadecyl-6-hydroxyphenyl)(2,5-dimethoxyphenyl) methanone 4a

The title compound was synthesized following the general procedure starting from [2-(benzyloxy)-6-pentadecylphenyl](2,5-dimethoxyphenyl)methanone 3a (217 mg, 384 μmol) using Pd/C (10 wt %, 22.0 mg, 20.1 μmol) and MeOH/EtOAc (10/1, 15 mL). The product 4a was obtained as a brownish solid (181 mg, 380 μmol, 99%). Mp. 45-47° C.; IR ($\tilde{v}$/cm$^{-1}$): 3362, 2922, 2852, 1606, 1582, 1494, 1463, 1278, 1223, 1046, 813, 722; $^1$H NMR (300 MHz, Chloroform-d) δ 9.32 (s, 1H, OH), 7.30 (dd, J=7.5, 8.3 Hz, 1H, H4'), 7.01 (dd, J=9.0, 3.1 Hz, 1H, H4), 6.91-6.85 (m, 3H, H3, H6, H5'), 6.69 (dd, J=7.5, 1.2 Hz, 1H, H3'), 3.74 (s, 3H, C5-OCH$_3$), 3.70 (s, 3H, C2-OCH$_3$), 2.26 (dd, J=9.8, 6.3 Hz, 2H, H1''), 1.34-1.14 (m, 26H, H2''-H14''), 0.88 (t, J=6.5 Hz, 3H, H15'') ppm; C NMR (76 MHz, Chloroform-d) δ 200.9 (C=O), 160.3 (C6'), 153.4 (C5), 151.5 (C2), 145.0 (C2'), 134.0 (C4'), 131.2 (C1'), 122.6 (C1'), 121.6 (C3'), 118.2 (C4), 115.4 (C5'), 114.4 (C6), 113.2 (C3), 56.4 (C2-OCH$_3$), 55.8 (C5-OCH$_3$), 34.7 (C1''), 32.4 (C2''), 31.9 (C13''), 29.7 (6C), 29.6, 29.5, 29.4, 29.3, 22.7 (C14''), 14.1 (C15'') ppm; MS (ESI+): m/z (%)=469.4 (100) [M+H]$^+$, 491.4 (16) [M+Na]$^+$; HRMS (ESI+). Found (M+H)$^+$ 469.3303. C$_{30}$H$_{45}$O$_4$ (M+H)$^+$ requires 469.3312.

(2-Pentadecyl-6-hydroxyphenyl)(2,4,5-trimethoxyphenyl) methanone 4b

The title compound was synthesized following the general procedure starting from [2-(benzyloxy)-6-pentadecylphenyl](2,4,5-trimethoxyphenyl)methanone 3b (243 mg, 413 μmol) using Pd/C (10 wt %, 25.0 mg, 23.5 μmol) and MeOH/EtOAc (10/1, 20 mL). The product 4b was obtained as a brownish solid (190 mg, 381 μmol, 92%). Mp. 78-81° C.; IR ($\tilde{v}$/cm$^{-1}$): 3314, 2922, 2852, 1581, 1513, 1462, 1354, 1270, 1212, 1025, 807; $^1$H NMR (300 MHz, Chloroform-d) δ 9.18 (s, 1H, OH), 7.25 (t, J=7.9 Hz, 1H, 4'), 7.02 (s, 1H, H6), 6.84 (dd, J=8.2, 1.1 Hz, 1H, H5'), 6.71 (dd, J=7.6 1.1 Hz, 1H, H3'), 6.49 (s, 1H, H3), 3.96 (s, 3H, C2-OCH$_3$/C4-OCH$_3$), 3.82 (s, 3H, C5-OCH$_3$), 3.68 (s, 3H4, C2-OCH$_3$/C4-OCH$_3$), 2.36-2.30 (m, 2H, H1''), 1.36-1.12 (m, 26H, H2''-H14''), 0.88 (t, J=7.0 Hz, 3H, H15'') ppm; $^{13}$C NMR (76 MHz, Chloroform-d) δ 198.7 (C=O), 158.1 (C6'), 154.1 (C2/C4), 153.7 (C2/C4), 143.9 (C2'), 143.2 (C5), 132.8 (C4'), 124.6 (C1'), 121.4 (C3), 121.4 (C1), 114.9 (C5), 113.1 (C6), 97.2 (C3), 56.6 (C2-OCH$_3$/C4-OCH$_3$), 56.5 (C5-OCH$_3$), 56.1 (C2-OCH$_3$/C4-OCH$_3$), 34.4 (C1''), 32.2 (C2''), 31.9 (C13'), 29.7 (6C), 29.5 (2C), 29.3 (2C), 22.7 (C14''), 14.1 (C15'') ppm; MS (ESI+): m/z (%)=499.5 (100) [M+H]$^+$, 521.4 (6) [M+Na]$^+$; HRMS (ESI+). Found (M+H)$^+$ 499.3409. C$_{32}$H$_{47}$O$_5$ (M+H)$^+$ requires 499.3418.

[2-(Hydroxy)-6-pentadecylphenyl](2-hydroxyphenyl) methanone 4c

The title compound was synthesized following the general procedure starting from [2-(benzyloxy)-6-pentadecylphenyl](2-benzyloxyphenyl)methanone 3c (44.6 mg, 74.0 μmol) using Pd/C (10 Wt %, 5.00 mg, 4.70 μmol) and MeOH/EtOAc (10/1, 4 mL). The product 4c was obtained as a yellowish oil (26.3 mg, 61.9 μmol, 84%). IR ($\tilde{v}$/cm$^{-1}$): 3392, 2923, 2853, 1625, 1583, 1463, 1307, 1283, 1110, 939, 756; $^1$H NMR (300 MHz, Chloroform-d) δ 12.07 (s, 1H, C2-OH), 7.48 (ddd, J=8.5, 7.2, 1.7 Hz, 1H, H4), 7.31 (dd, J=8.0, 1.7 Hz, 1H, H6), 7.25 (t, J=7.9 Hz, 1H, H4'), 7.03 (dd, J=8.5, 1.1 Hz, 1H, H3), 6.87 (d, J=7.7 Hz, 1H, H3), 6.83-6.79 (m, 11H, H5), 6.73 (dd, J=8.2, 1.0 Hz, 1H, H3'), 5.69 (s, 1H, C2'-OH), 2.42 (dd, J=9.0, 6.7 Hz, 2H, H1''), 1.45 (p, J==6.8 Hz, 2H, H2''), 1.33-1.14 (m, 24H, H3''-H14''), 0.86 (t, J=6.7 Hz, 3H, H15'') ppm; $^{13}$C NMR (76 MHz, Chloroform-d) δ 203.8 (C=O), 162.7 (C2), 152.8 (C2'), 142.0 (C6'), 137.0 (C4), 133.2 (C6), 131.0 (C4'), 125.1 (C1'), 121.8 (C5'), 120.7 (C1), 119.2 (C5), 118.2 (C3), 113.8 (C3'), 33.5 (C1''), 31.9 (C13''), 31.1 (C2''), 29.7 (3C), 29.6 (3C), 29.4, 29.3, 29.2 (2C), 22.7 (C14''), 14.1 (C15'') ppm; MS (ESI–): m/z (%) 423.4 (100)) [M–H]$^+$; HRMS (ESI+). Found (M+H)$^+$ 425.3047, C$_{28}$H$_{41}$O$_3$ (M+H)$^+$ requires 425.3050.

(2-Hydroxy-5-methoxyphenyl)(2-hydroxy-6-pentadecylphenyl)methanone 5

AlCl$_3$ (9.05 mg, 67.9 μmol) and pyridine (16.4 μL, 203.6 μmol) were added to a solution of (2-pentadecyl-6-hydroxyphenyl)(2,5-dimethoxyphenyl)methanone (15.9 mg, 33.9 μmol) in dry toluene (1 mL) at room temperature under an atmosphere of nitrogen. The resulting solution was stirred for 5 d under reflux and each day AlCl$_3$ (9.05 mg, 67.9 μmol) and pyridine (16.4 μL, 203.6 μmol) were added. The mixture was cooled to room temperature afterwards. Aqueous HCl (2 m, 5 mL) was added and the mixture was extracted with diethyl ether (3×5 mL). The combined organic extracts were dried over Na$_2$SO$_4$ and evaporated. The crude product was purified by column chromatography on silica gel (17% EtOAc/cyclohexane) to obtain the product as a brown oil 5 (8.60 mg, 18.9 μmol, 56%). IR ($\tilde{v}$/cm$^{-1}$): 3377, 2922, 2853, 1612, 1484, 1463, 1284, 1040, 791; $^1$H NMR (300 MHz, Chloroform-d) δ 11.68 (s, 1H, C2'-OH), 7.27 (t$_{app}$, J$_{app}$=7.9 Hz, 1H, H4), 7.13 (dd, J=9.1, 3.0 Hz, 1H, H4'), 7.00 (d, J=9.1 Hz, 1H, H3'), 6.88 (d, J=7.5 Hz, 1H, 1H5), 6.76 (m, 2H, H3, H6'), 5.59 (s, br, 1H, C2-OH), 3.63 (s, 3H, C5'-OCH$_3$), 2.46-2.43 (m, 2H, H1''), 1.49-1.44 (m, 2H, H2''), 1.25-1.15 (m, 24H, H3''-H14''), 0.88 (t, J=6.7 Hz, 3H, H15'') ppm; $^{13}$C NMR (76 MHz, Chloroform-d) δ 203.3 (C=O), 157.2 (C2'), 152.9 (C2), 151.9 (C5), 142.1 (C6), 131.2 (C4), 124.9 (2C, C1, C4'), 121.9 (C5), 120.3 (C1'), 119.2 (C3'), 115.4 (C6'), 113.9 (C3), 55.8 (C5'-OCH$_3$), 33.6 (C1''), 31.9 (C13''), 31.2 (C2''), 29.7 (4C), 29.6 (2C), 29.4 (2C), 29.2 (2C), 22.7 (C14''), 14.1 (C15'') ppm; MS (ESI+): m/z (%)=455.4 (100) [M+H]$^+$, 477.3 (37) [M+Na]$^+$; HRMS (ESI+). Found (M+H)$^+$ 455.3159. C$_{29}$H$_{43}$O$_4$ (M+H)$^+$ requires 455.3156.

(2-Pentadecyl-6-hydroxyphenyl)(2-hydroxy-4,5-dimethoxyphenyl)methanone 6

A solution of BCl$_3$ in CH$_2$Cl$_3$ (1 m, 29.0 μL, 29.0 μmol) was added to a solution of (2-pentadecyl-6-hydroxyphenyl) (2,4,5-trimethoxyphenyl)methanone 4b (13.3 mg, 26.7 μmol) in dry CH$_2$Cl$_2$ at −78° C. under an atmosphere of nitrogen while stirring. The solution was kept at this temperature for 8 h and then brought to rt overnight. Stirring was continued for 4 d at rt and each day $BCl_3$ in $CH_2Cl_7$ (1 M, 29.0 µL, 29.0 µmol) was added. Aqueous NaOH (1 m, 1 mL) was added and the mixture was stirred for 1 h. Then aqueous HCl (2 m, 1 mL) was added and the mixture was extracted with $CH_2Cl_2$ (2×3 mL). The combined organic extracts were dried over $Na_2SO_4$ and evaporated. The crude product was purified by column chromatography on silica gel (25% EtOAc/cyclohexane) to obtain (2-pentadecyl-6-hydroxyphenyl)(2-hydroxy-4,5-dimethoxyphenyl)methanone as a yellow solid 6 (8.90 mg, 18.3 µmol, 69%). Mp. 86.3-88° C.; IR ($\tilde{v}$/cm$^{-1}$): 3439, 2922, 2852, 1626, 1441, 1238, 1204, 1164, 1126, 800; $^1$H NMR (300 MHz, Chloroform-d) δ 12.58 (s, 1H, C2-OH), 7.27 (t$_{app}$, J$_{app}$=7.9 Hz, 1H, H4'), 6.88 (dd, J=7.7, 1.0 Hz, 1H, H3'), 6.79 (dd, J=8.1, 1.0 Hz, 1H, H5'), 6.65 (s, 11H, H6), 6.52 (s, 1H, H3), 5.78 (s, br, 1H, C6'-OH), 3.94 (s, 3H, C4-OCH$_3$), 3.62 (s, 3H, C5-OCH$_3$), 2.47 (t, J=7.8 Hz, 2H, H1"), 1.50-1.42 (m, 2H, H2"), 1.30-1.16 (m, 24H, H3"-H14"), 0.86 (t, J=6.9 Hz, 3H, H15") ppm; $^{13}$C NMR (76 MHz, Chloroform-d) δ 200.8 (C=O), 161.0 (C2), 157.6 (C4), 153.0 (C6'), 142.2 (C5), 141.8 (C2'), 131.1 (C4'), 125.0 (C1'), 121.8 (C3'), 114.0 (C5'), 113.4 (C6), 112.8 (C1), 100.5 (C3), 56.4 (C5-OCH$_3$), 56.3 (C4-OCH$_3$), 33.6 (C1"), 31.9 (C13"), 31.3 (C2"), 29.7 (5C), 29.6 (2C), 29.5, 29.4, 29.3, 22.7 (C14"), 14.1 (C15") ppm; MS (ESI+): m/z (%)=485.4 (100) [M+H]$^+$, 507.3 (22) [M+Na]$^+$; HRMS (ESI+). Found (M+H)$^+$ 485.3258, $C_{20}H_{45}O_5$ (M+H)$^+$ requires 485.3262.

3-Pentadecylphenyl benzoate 8

To a stirred solution of 3-pentadecylphenol 7 (5.00 g, 16.42 mmol) in 2-Methyl-THF (60 mL), triethylamine (4.58 mL, 32.84 mmol) and 4-dimethylaminopyridine (0.200 g, 1.64 mmol) was added and the mixture cooled to 0° C. To this cooled mixture, benzoyl chloride (2.54 g, 2.10 mL, 18.06 mmol) dissolved in 2-Methyl-THF (20 mL) was slowly added and the reaction mixture was warmed to it and stirred for 2 h. upon completion, the reaction was quenched with water (50 mL) and the mixture extracted with EtOAc (3×100 mL). The combined organic extracts were washed with aq. NaHCO$_3$ (100 mL) followed by brine (100 mL) and then dried over MgSO$_4$ and the solvent removed under reduced pressure. The crude product was purified by column chromatography on silica gel (10% EtOAc/cyclohexane) to afford the 3-pentadecylphenyl benzoate 8 as a white crystalline solid (5.96 g, 89%). Mp. 52.1-53.9° C.; IR ($\tilde{v}$/cm$^{-1}$): 2918, 2846, 1731, 1585, 1238, 1144, 1079, 710; $^1$H NMR (400 MHz, Chloroform-d) δ 8.25 (dd, J=8.3, 1.4 Hz, 2H, H2'), 7.69-7.64 (m, 1H, H4'), 7.55 (dd, J=8.3, 7.0 Hz, 2H, H3'), 7.36 (td, J=7.6, 1.5 Hz, 1H, H5), 7.13 (dd, J=7.7, 1.3 Hz, 1H, H4), 7.10-7.05 (m, 2H, H2, H6), 2.68 (t, J=7.7 Hz, 2H, H1"), 1.75-1.63 (m, 2H, H2"), 1.30 (m, 24H, H3"-H14"), 0.92 (t, J=5.7 Hz, 3H, H15") ppm; $^{13}$C NMR (101 MHz, Chloroform-d) δ 165.2 (C=O), 151.0 (C1), 144.8 (C3), 133.5 (C4'), 130.2 (C2'), 129.7 (C1'), 129.2 (C5), 128.5 (C3'), 126.0 (C4), 121.6 (C2), 118.8 (C5), 35.8 (C1"), 32.0 (C13"), 31.3 (C2"), 29.7 (6C), 29.6 (1C), 29.5 (1C), 29.4 (1C), 29.3 (1C), 22.7 (C14"), 14.2 (C15") ppm; HRMS (ESI+). Found (M+H) 409.3107, $C_{28}H_{41}O_2$ (M+H)$^+$ requires 409.3101.

(2-Hydroxy-4-pentadecylphenyl)(phenyl)methanone 9

3-Pentadecylphenyl benzoate 8 (0.20 g, 0.49 mmol) was dissolved in chlorobenzene (3 mL) in a microwave reactor tube. To this solution. AlCl$_3$, (0.16 g, 1.23 mmol) was added. The tube was sealed and the reaction mixture was subjected to microwave irradiation (150 W, 160° C.) for 30 min. After cooling to rt, the crude product was purified by column chromatography (5% EtOAc/cyclohexane) to afford (2-hydroxy-4-pentadecylphenyl)(phenyl)methanone 9 as an off-white solid (0.16 g, 78%). Mp. 40.8-42.6° C.; IR ($\tilde{v}$/cm$^{-1}$): 2912, 2848, 1626, 1600, 1470, 1334, 1223, 915, 765, 700; $^1$H NMR (400 MHz, Chloroform-d) δ 12.19 (s, 1H, C2-OH), 7.72-7.67 (m, 2H, H2'), 7.62-7.56 (m, 1H, H4'), 7.54-7.50 (m, 3H, H3' and H6), 6.93 (d, J==1.6 Hz, 1H, H3), 6.72 (dd, J=8.2, 1.7 Hz, 1H, 1H5), 2.65 (t, 2H, H1"), 1.73-1.60 (m, 2H, H2"), 1.30 (m, 24H, H3"-H14"), 0.91 (t, J=5.6 Hz, 3H, H15") ppm; $^{13}$C NMR (101 MHz, Chloroform-d) δ 201.1 (C=O), 163.5 (C2), 153.0 (C4), 138.2 (C1'), 133.5 (C6), 131.7 (C4'), 129.1 (C2'), 128.3 (C3'), 119.5 (C5), 117.8 (C3), 117.1 (C1), 36.3 (C1"), 32.0 (C13"), 30.7 (C2") 29.7 (6C), 29.6 (1C), 29.5 (1C), 29.4 (1C), 29.3 (1C), 22.7 (C14"), 14.2 (C15") ppm; HRMS (ESI+). Found (M+H)$^+$ 409.3096, $C_{28}H_{41}O_2$ (M+H)$^+$ requires 409.3101.

(2-hydroxy-4-pentadecylphenyl)(2-hydroxyphenyl)methanone 10

To a 15 mL scintillation vial were added (2-hydroxy-4-pentadecylphenyl)(phenyl)methanone 9 (0.30 g, 0.73 mmol), $K_2S_2O$ % (0.40 g, 1.47 mmol), [Ru(p-cymene)Cl$_2$]$_2$ (11 mg, 0.018 mmol). TFAA (5.0 mL) and TFA (2.0 mL). The reaction was scaled with a Teflon-lined cap and heated at 80° C. and was monitored by TLC. After completion, EtOAc was added to dilute the reaction mixture and saturated aqueous NaHCO$_3$ was added to neutralize TFA and TFAA. Then the organic layer was dried over anhydrous Na$_2$SO$_4$ and concentrated in vacuo. Finally, the residue was purified by silica gel column chromatography (5% EtOAc/hexane) to give (2-hydroxy-4-pentadecylphenyl)(2-hydroxyphenyl)methanone 10 as a white crystalline solid (220 mg, 72%). Mp. 31.4-32.6° C.; IR ($\tilde{v}$/cm$^{-1}$): 3403, 2921, 2852, 1599, 1573, 1337, 1229, 755, 699; $^1$H NMR (300 MHz, Chloroform-d) δ 10.86 (s, 1H, C2-OH), 10.52 (s, 1H, C2'-OH), 7.61 (dd, J=8.0, 1.8 Hz, 1H, H6'), 7.56-7.41 (m, 2H, H4' and H6), 7.07 (d, J=8.4 Hz, 1H, H3'), 6.93 (d, J=7.7 Hz, 1H, H5'), 6.89 (s, 1H, H3), 6.74 (dd, J=8.3, 1.8 Hz, 1H, H5), 2.62 (t, 2H, H1"), 1.67-1.61 (m, 2H, H2"), 1.26 (m, 24H, H3"-H14"), 0.87 (t, J=5.7 Hz, 3H, H15") ppm; $^{13}$C NMR (75 MHz, Chloroform-d) δ 201.8 (C=O), 162.3 (C2), 161.4 (C2'), 152.8 (C4), 135.5 (C4'), 133.1 (C6), 132.9 (C6'), 120.1 (C1'), 119.5 (C5), 118.7 (C5'), 118.5 (C3'), 118.0 (C3), 117.5 (C1), 36.2 (C1"), 31.9 (C13"), 30.6 (C2"), 29.7 (6C), 29.6 (1C), 29.5 (1C), 29.4 (1C), 29.3 (1C), 22.7 (C14"), 14.1 (C15") ppm; HRMS (ESI+). Found (M+H)$^+$ 425.3058, $C_{28}H_{42}O_4$ (M+H)$^+$ requires 425.3050.

3-Pentadecylphenyl Acetate 11

To a stirred solution of 3-pentadecylphenol 7 (2.00 g, 6.57 mmol) in 2-Methyl-THF (20 mL), triethylamine (1.83 mL, 13.14 mmol) and 4-dimethylaminopyridine (0.08 g, 0.66 mmol) was added and the mixture cooled to 0° C. To this cooled mixture, acetyl chloride (0.62 g, 0.56 mL, 7.88 mmol) dissolved in 2-Methyl-THF (5 mL) was slowly added and the reaction mixture was slowly warmed to rt and stirred at rt for 2 h. The reaction was quenched with water (20 mL) and the mixture extracted with EtOAc (3×50 mL). The combined organic extracts were washed with aq. NaHCO$_3$ (50 mL) followed by brine (50 mL) and then dried over MgSO$_4$ and the solvent removed under reduced pressure. The crude product was purified by column chromatography on silica gel (10% EtOAc/cyclohexane) to afford the 3-pentadecylphenyl acetate 11 as a low melting white solid (2.15 g, 93%), Mp. 36.9-37.5° C.; IR ($\tilde{v}$/cm$^{-1}$): 2914, 2848, 1757, 1612, 1587, 1204, 1142, 1015, 952, 694; $^1$H NMR (400 MHz, Chloroform-d) 7.34-7.27 (m, 1H, H5), 7.09 (d, J=7.7 Hz, 1H, 1H, H4), 6.96 (d, J=1.3 Hz, 1H, H2), 6.97-6.93 (m, 1H, H6), 2.66 (t, 2H, H1"), 2.32 (s, 3H, H1'), 1.73-1.60 (m, 2H, H2") 1.32 (m, 24H, H3"-H14"), 0.94 (t, J=5.7 Hz, 3H, H15″) ppm; $^{13}$C NMR (101 MHz, Chloroform-d) δ 169.5 (C=O), 150.7 (C1), 144.7 (C3), 129.1 (C5), 125.9 (C4), 121.4 (C2), 118.7 (C6), 35.8 (C1″), 32.0 (C13″), 31.3 (C2″), 29.8 (5C) 29.7 (1C), 29.6 (1C), 29.5 (1C), 29.4 (1C), 29.3 (0C), 22.8 (C14″), 21.1 (C1′), 14.2 (C15″) ppm; HRMS (ESI+). Found (M+Na)$^+$ 369.2761, $C_{23}H_{38}O_2Na$ (M+Na)$^+$ requires 369.2764.

1-(2-Hydroxy-4-pentadecylphenyl)ethanone 12

3-Pentadecylphenyl acetate 11 (0.40 g, 1.16 mmol) was dissolved in chlorobenzene (6 mL) in a microwave reactor tube. To this solution. $AlCl_3$ (0.38 g, 2.88 mmol) was added. The tube was sealed and the reaction mixture was subjected to microwave irradiation (150 W, 160° C.) for 30 min. After cooling, the crude product was purified by column chromatography (10% EtOAc/cyclohexane) to afford 1-(2-hydroxy-4-pentadecylphenyl)ethanone 12 as a light brown solid (0.39 g, 99%). Mp. 49.1-50.5° C.; IR ($\tilde{v}$/cm$^{-1}$): 2915, 2848, 1636, 1573, 1471, 1365, 1249, 799, 717; $^1$H NMR (400 MHz, Chloroform-d) δ 12.31 (s, C2′-OH), 7.65 (d, J=8.2 Hz, 1H, H6′), 6.81 (d, J=1.6 Hz, 1H, H3′), 6.74 (dd, J=8.2, 1.7 Hz, 1H, H5′), 2.67-2.54 (m, 5H, H1 and H1″), 1.70-1.57 (m, 2H, H2″), 1.40-1.20 (m, 24H, H3″-H14″), 0.89 (t, J=5.5 Hz, 3H, H15″) ppm; $^{13}$C NMR (101 MHz, Chloroform-d) δ 203.8 (C=O), 162.5 (C2′), 153.0 (C4′), 130.6 (C6′), 119.6 (C5′), 117.7 (C3′), 36.2 (C1″), 31.9 (C13″), 30.7 (C2″), 29.7 (6C), 29.6 (1C), 29.5 (1C), 29.4 (1C), 29.3 (1C), 26.5 (C1), 22.7 (C14″), 14.1 (C15″) ppm; HRMS (ESI+). Found (M+H)$^+$ 347.2942, $C_{23}H_{39}O_2$ (M+H)$^+$ requires 347.2945. The data is consistent with what has been reported in literature. [24]

(E)-1-(2-hydroxy-4-pentadecylphenyl)-3-phenylprop-2-en-1-one 13a

To a round-bottom flask (10 mL), equipped with magnetic stirrer were added 1-(2-hydroxy-4-pentadecylphenyl)ethanone 12 (0.097 g, 0.28 mmol), benzaldehyde (28 μL, 30 mg, 0.28 mmol), sodium hydroxide (34 mg, 0.85 mmol) and methanol (2 mL). The pale yellow mixture was refluxed until the colour was turned into orange (about 4 h). The mixture was poured into ice-water and extracted with ethyl acetate (3×10 mL). The organic layer was dried over $Na_2SO_4$, filtered and the solvent was removed in vacuo. The crude product was subjected to column chromatography (5% EtOAc/cyclohexane) to furnish ((E)-1-(2-hydroxy-4-pentadecylphenyl)-3-phenylprop-2-en-1-one 13a as a bright yellow solid (0.085 g, 67%). Mp. 54.7-56.4° C.; IR ($\tilde{v}$/cm$^{-1}$): 2915, 2849, 1640, 1618, 1350, 1204, 1148, 788, 738; $^1$H NMR (400 MHz, Chloroform-d) δ 12.91 (s, 1H, C2″-OH), 7.93 (d, J=15.5 Hz, 1H, 113), 7.85 (d, J=8.3 Hz, 11H, H6″), 7.71-7.63 (m, 3H, H2 and H2′), 7.50-7.43 (m, 3H, H3′ and H4′), 6.87 (d, J=1.5 Hz, 1H, H3″), 6.79 (dd, J=8.2, 1.7 Hz, 1H, H5″), 2.64 (t, 2H, H1‴), 1.90-1.47 (m, 2H, H2″), 1.28 (m, 24H, H3‴-H14‴) 0.90 (t, J=5.7, 3H, H15‴) ppm; $^{13}$C NMR (101 MHz, Chloroform-d) δ 193.1 (C=O), 163.8 (C2″), 153.1 (C4″), 144.9 (C3), 134.7 (C1′), 130.8 (C4′), 129.5 (C6″), 129.0 (C3′), 128.6 (C2′), 120.3 (C2), 119.5 (C5″), 118.0 (C3″) 36.3 (C1‴) 31.9 (C13‴) 30.7 (C2‴) 29.7 (6C), 29.6 (1C), 29.5 (1C), 29.4 (1C), 29.3 (1C), 22.7 (C14‴), 14.1 (CIS‴) ppm; HRMS (ESI+): Found (M+H)$^+$ 435.3259, $C_{30}H_{43}O_2$(M+H)$^+$ requires 435.3258.

3-Hydroxy-7-pentadecyl-2-phenyl-4H-chromen-4-one 13b ((E)-1-(2-hydroxy-4-pentadecylphenyl)-3-phenylprop-2-en-1-one (0.156 g, 0.36 mmol) was dissolved in methanol (10 mL) in a 50 mL round-bottom flask. To this stirring mixture, sodium hydroxide (0.5 N, 2.7 mL) and hydrogen peroxide (30%, 220 μL) were added and the mixture was stirred at rt for 2 h upon which the colour changed to orange. The reaction was acidifies with aqueous HCl (15 mL) and the mixture extracted with ethyl acetate (3×20 mL). The organic layer was dried over $Na_2SO_4$, filtered and the solvent was removed under reduced pressure. The crude product was subjected to column chromatography (10% EtOAc/hexane) to give 3-hydroxy-7-pentadecyl-2-phenyl-4H-chromen-4-one 13b as a yellow solid (0.141 g, 88%). Mp. 81.2-83.7° C.; IR ($\tilde{v}$/cm$^{-1}$): 3406, 2918, 2841, 1643, 1612, 1363, 1203, 1149, 747; $^1$H NMR (500 MHz, Chloroform-d) δ 8.26 (dd, J=8.8, 1.5 Hz, 2H, H2′), 8.15 (d, J=8.1 Hz, 1H, H5), 7.54 (t, J=7.6, Hz, 2H, H3′), 7.50-7.44 (m, 1H, H4′), 7.40 (d, J=1.4 Hz, 1H, H8), 7.28-7.22 (m, 2H, H6 and C3-OH), 2.76 (t, J=7.7, Hz, 1H, H1″), 1.75-1.65 (m, 1H, H2″), 1.41-1.20 (m, 24H, H3″-H14″), 0.88 (t, J=6.9. Hz, 3H, H15″) ppm; $^{13}$C NMR (126 MHz, Chloroform-d) δ 173.4 (C=O), 155.7 (C8a), 150.1 (C7), 144.5 (C2), 138.3 (C3), 131.3 (C1′), 130.0 (C4′), 128.6 (C3′), 127.7 (C2′), 125.6 (C6), 125.2 (C5), 118.6 (C4a), 117.3 (C8), 36.2 (C1″), 31.9 (C13″), 30.9 (C2″), 29.7 (5C), 29.6 (1C), 29.5 (2C), 29.4 (1C), 29.2 (1C), 22.7 (C14″), 14.1 (C15″) ppm; HRMS (ESI+). Found (M+H)$^+$ 449.3054. $C_{30}H_{43}O_3$ (M+H)$^+$ requires 449.3050.

3-Pentadecylphenyl-2-fluorobenzoate 15

To a stirred solution of 3-pentadecylphenol 7 (2.07 g, 6.69 mmol) in 2-Methyl-THF (20 mL), triethylamine (1.37 g, 1.89 mL, 13.58 mmol) and 4-dimethylaminopyridine (0.083 g, 0.68 mmol) was added and the mixture cooled to 0° C. To this cooled mixture, 2-fluorobenzoyl chloride (1.19 g, 0.89 mL, 7.48 mmol) dissolved in 2-Methyl-THF (5 mL) was slowly added and the reaction mixture was slowly warmed to rt and stirred at rt for 2 h. The reaction was quenched with water (20 mL) and the mixture extracted with EtOAc (3×50 mL). The combined organic extracts were washed with aq. $NaHCO_3$ (50 mL) followed by brine (500 mL) and then dried over $MgSO_4$ and the solvent removed under reduced pressure. The crude product was purified by column chromatography on silica gel (10% EtOAc/cyclohexane) to afford the 3-pentadecylphenyl-2-fluorobenzoate 15 as a white crystalline solid (2.84 g, 98%). Mp. 57.2-58.9° C.; IR ($\tilde{v}$/cm$^{-1}$): 2932, 2813, 1702, 1596, 1214, 1130, 1081, 747, 712; $^1$H NMR. (400 MHz, Chloroform-d) δ 8.14 (td, J=7.5, 7.5, 1.8 Hz, 1H, H6′), 7.68-7.57 (m, 1H, H4′), 7.36 (td, J=7.4, 7.4, 1.3 Hz, 1H, H5), 7.35-7.26 (m, 1H, 15′), 7.24 (ddd, J=10.8, 8.3, 1.1 Hz, 1H, H3′), 7.13 (dd, J=7.7, 1.3 Hz, 1H, H4), 7.10 (d, J=1.3 Hz, 1H, H2), 7.09-7.06 (m, 1H, H6), 2.68 (t, 2H, H1″), 1.73-1.62 (m, 2H, H2″), 1.31 (m, 24H, H3″-H14″), 0.92 (t, J=5.7 Hz, 3H, H15″) ppm; $^{13}$C NMR (101 MHz, Chloroform-d) δ 163.6 (C=O), 162.9 (C2′), 162.8 (C2′), 161.0 (C2′), 150.6 (C1), 144.8 (C3), 135.1 (C4′), 132.5 (C6′), 129.2 (C5), 126.1 (C4), 124.1 (C5′), 124.1, 121.5 (C2), 118.8 (C6), 117.3 (C1′), 117.1 (C3′), 35.8 (C1″), 32.0 (C13″), 31.3 (C2″), 29.7 (6C), 29.6 (1C), 29.5 (1C), 29.4 (1C), 29.3 (1C), 22.8 (C14″), 14.2 (C15″) ppm; HRMS (ESI+). Found (M+Na)$^+$ 449.2881. $C_{28}H_{39}FNaO_2$ (M+Na)$^+$ requires 449.2886.

(2-Fluorophenyl)(2-hydroxy-4-pentadecylphenyl)methanone 16

3-Pentadecylphenyl-2-fluorobenzoate 15 (0.101 g, 2.37 mmol) was dissolved in chlorobenzene (12 mL) in a microwave reactor tube. To this solution, $AlCh_3$ (0.79 g, 5.92 mmol) was added. The tube was scaled and the reaction mixture was subjected to microwave irradiation (150 W, 160° C.) for 30 min. After cooling, the crude product was purified by column chromatography (5% EtOAc/cyclohexane) to afford (2-fluorophenyl)(2-hydroxy-4-pentadecylphenyl)methanone 16 as an off-white solid (0.85 g, 84%). Mp. 41.4-43.2° C.; IR ($\tilde{v}$/cm$^{-1}$): 2916, 2846, 1614, 1454, 1333, 1217, 1162, 914, 759; $^1$H NMR (400 MHz, Chloroform-d) δ 12.09 (s, OH, C2-OH), 7.58-7.43 (m, 2H, H4' and H6'), 7.38-7.25 (m, 2H, H3' and H6), 7.21 (ddd, J=9.5, 8.3, 1.0 Hz, 1H, H5'), 6.91 (d, J=1.6 Hz, 1H, H3), 6.71 (dd, J=8.3, 1.7 Hz, 1H, H5), 2.64 (t, 2H, H1"), 1.74-1.59 (m, 2H, H2"), 1.30 (m, 24H, H3"-H14"), 0.91 (t, J=5.8 Hz, 31H, H15") ppm; $^{13}$C NMR (101 MHz, Chloroform-d) δ 197.8 (C=O), 163.3 (C2-OH), 160.3 (C2'), 157.8 (C1'), 153.8 (C4), 133.3 (C6), 132.7 (C6'), 129.8 (C4'), 128.6 (C1), 124.4 (C3'), 119.7 (C4), 117.7 (C3), 116.1 (C5'), 36.4 (C1"), 32.0 (C13"), 30.6 (C2"), 29.8 (6C), 29.6 (1C), 29.5 (1C), 29.4 (1C), 29.3 (1C), 22.7 (C14"), 14.2 (C15") ppm; HRMS (ESI+). Found (M+H)$^+$ 427.3002, $C_{28}H_{40}FO_2$ (M+H)$^+$ requires 427.3007.

3-Pentadecyl-9H-xanthen-9-one 17

To a 25 mL round bottom flask were added (2-fluorophenyl)(2-hydroxyphenyl)methanone 16 (0.225 g, 0.53 mmol), $K_2CO_3$ (0.146 g, 1.05 mmol) and 5 mL of acetone at rt. The reaction mixture was heated at 50° C. for 4 h. The resulting mixture was allowed to cool to rt, the filtered and then extracted with $CH_2Cl_2$. The organic layer was dried over anhydrous $Na_2SO_4$ and the solvent was concentrated in vacuo. Finally, the residue was purified by silica gel column chromatography (5% EtOAc/cyclohexane) to give the desired 3-pentadecyl-9H-xanthen-9-one 17 as a white solid (0.183 g, 86%). Mp. 75.2-76.4° C.; IR ($\tilde{v}$/cm$^{-1}$): 2915, 2848, 1663, 1606, 1463, 1431, 1344, 1179, 1149, 1109, 959, 758, 727; $^1$H NMR (400 MHz, Chloroform-d) δ 8.34 (dd, J=7.9, 1.7 Hz, 1H, H8), 8.24 (d, J=8.2 Hz, 1H, H1), 7.70 (ddd, J=8.7, 7.1, 1.8 Hz, 1H, H6), 7.47 (dd, J=8.5, 1.0 Hz, 1H, H5), 7.36 (ddd, J=8.1, 7.1, 1.1 Hz, 1H, H7), 7.28 (d, J=1.3 Hz, 1H, H4), 7.20 (dd, J=8.2, 1.6 Hz, 1H, H2), 2.75 (t, 2H, H1'), 1.76-1.64 (m, 2H, H2'), 1.40-1.19 (m, 24H, H3'-H14'), 0.88 (t, J=5.8 Hz, 3H, H15') ppm; $^{13}$C NMR (101 MHz, Chloroform-d) δ 177.0 (C=O), 156.3 (C4a), 156.1 (C10a), 151.3 (C3), 134.5 (C6), 126.7 (C5), 126.5 (C1), 124.8 (C2), 123.7 (C7), 121.9 (C8a), 119.8 (C9a), 117.9 (C5), 117.0 (C4), 36.2 (C1'), 31.9 (C13'), 30.9 (C2'), 29.7 (6C), 29.6 (1C), 29.5 (1C), 29.4 (1C), 29.3 (1C), 22.7 (C14'), 14.1 (C15') ppm; HRMS (ESI+). Found (M+H)$^+$ 407.2940. $C_{28}H_{39}O_2$ (M+H)$^+$ requires 407.2945.

1,8-Dihydroxy-3-pentadecyl-9H-xanthen-9-one 14

To a 25 mL scintillation vial were added 3-pentadecyl-9H-xanthen-9-one 16 (0.54 g, 1.32 mmol), $K_2S_2O_8$ (1.44 g, 5.31 mmol). [Ru(p-cymene)Cl$_2$]$_2$ (11 mg, 20.2 mmol), TFAA (10.5 mL) and TFA (4.5 mL). The reaction was scaled with a Teflon-lined cap and heated at 80° C. and was monitored by TLC. After completion. EtOAc was added to dilute the reaction mixture and saturated aqueous NaHCO$_3$ was added to neutralize TFA and TFAA. Then the organic layer was dried over anhydrous Na$_2$SO$_4$ and concentrated in vacuo. Finally, the residue was purified by silica gel column chromatography (5% EtOAc/hexane) to give 1-hydroxy-3-pentadecyl-9H-xanthen-9-one 14 as a white crystalline solid (395 mg, 71%). Mp. 93.7-95.9° C.; IR ($\tilde{v}$/cm$^{-1}$): 3401, 2914, 2849, 1630, 1597, 1498, 1319, 1239, 1077, 1057, 831, 749, 736; $^1$H NMR (300 MHz, Chloroform-d) δ 12.56 (s, 1H, C1-OH), 8.27 (dd, J=8.0, 1.7 Hz, 1H, H8), 7.73 (ddd, J=8.7, 7.1, 1.7 Hz, 1H, H6), 7.45 (dd, J=7.5, 1.0 Hz, 1H, H5), 7.38 (ddd, J=8.1, 7.1, 1.0 Hz, 1H, H7), 6.77 (d, J=1.4 Hz, 1H, H2), 6.65 (d, J=1.4 Hz, 1H, H4), 2.67 (t, J=7.7, Hz, 2H, H1'), 1.77-1.56 (m, 2H, 1H2'), 1.31-1.19 (m, 24H, H3'-H14'), 0.88 (t, J=6.3 Hz, 311, 115') ppm; $^{13}$C NMR (76 MHz, Chloroform-d) δ 181.8 (C=O), 161.6 (C1), 156.2 (C4a), 156.2 (C10a), 154.0 (C3), 135.3 (C6), 126.0 (C5), 123.9 (C7), 120.7 (C8a), 117.8 (C5), 110.6 (C4), 107.2 (C9a), 106.8 (C2), 36.8 (C1', 1C, 3, 30.6 (C2'), 29.7 (6C), 29.5 (1C), 29.5 (1C), 29.4 (1C), 29.2 (1C), 22.7 (C14'), 14.1 (C15') ppm; HRMS (ESI+). Found (M+H) 423.2894, $C_{28}H_{39}O_3$ (M+H)$^+$ requires 423.2894. To a 15 mL scintillation vial were added some of the 1-hydroxy-3-pentadecyl-9H-xanthen-9-one (0.18 g, 0.43 mmol). $K_2S_2O_8$ (0.46 g, 1.70 mmol), [Ru(p-cymene)Cl$_2$]$_2$ (13.1 mg, 0.022 mmol). TFAA (5.0 mL) and TFA (2.0 mL). The reaction was sealed with a Teflon-lined cap and heated at 80° C. and was monitored by TLC. After completion. EtOAc was added to dilute the reaction mixture and saturated aqueous NaHCO$_3$ was added to neutralize TFA and TFAA. Then the organic layer was dried over anhydrous Na$_2$SO$_4$ and concentrated in vacuo. Finally, the residue was purified by silica gel column chromatography (5% EtOAc/hexane) to furnish 1,8-dihydroxy-3-pentadecyl-9H-xanthen-9-one 14 as off-white solid (121 mg 0.64%). Mp. 92.3-93.2° C.; IR ($\tilde{v}$/cm$^{-1}$): 2915, 2849, 1633, 1595, 1490, 1471, 1316, 1233, 1079, 1055, 831, 747, 732; $^1$H NMR (600 MHz, Chloroform-d) δ 11.92 (s, 1H, C8-OH), 11.75 (s, 1H, C1-OH), δ 7.61 (t, J=8.4, 8.4 Hz, 1H, H6), 6.91 (dd, J=8.4, 0.9 Hz, 1H, H5), 6.80 (dd, J=8.3, 0.9 Hz, 1H, H7), 6.77 (d, J=1.4 Hz, 1H, H4), 6.66 (d, J=1.4 Hz, 1H, H2), 2.69 (t, 2H, H1'), 1.75-1.64 (m, 2H, H2'), 1.39-1.24 (m, 24H, H3'-H14'), 0.89 (t, J=5.9 Hz, 3H, H15') ppm; $^{13}$C NMR (151 MHz, Chloroform-d) δ 185.7 (C=O %) 161.3 (C8), 161.0 (C1), 156.3 (C10a), 156.2 (C4a), 154.9 (C3), 137.2 (C6), 111.0 (C2), 110.7 (C7), 107.8 (C8a), 107.1 (C4), 107.1 (C5), 106.0 (C9a), 36.8 (C1'), 31.9 (C13'), 30.6 (C2'), 29.7 (5C), 29.6 (1C), 29.5 (1C), 29.4 (1C), 29.2 (1C), 26.9 (1C), 22.7 (C14'), 14.2 (C15') ppm; HRMS (ESI+): Found (M+H)° 439.2861, $C_{28}H_{39}O_4$ (M+H)$^+$ requires 439.2843.

2-Hydroxy-4-pentadecylbenzaldehyde 18

To a stirred mixture of 3-pentadecylphenol 7 (3.04 9, 9.85 mmol), tri-n-butylamine ((0.4 M), and tin tetrachloride (0.26 g, 0.1.15 mL, 0.96 mmol) in toluene (50 mL), at ambient temperature, paraformaldehyde (0.65 g, 21.67 mmol) was added and after 30 min the yellow solution was heated at 100° C. for 8 h. Then reaction mixture was then cooled and then poured into water acidified with 2 m HCl and extracted with diethyl ether. The ether extract, was washed with brine, dried over Na$_2$SO$_4$ and concentrated under reduced pressure. The crude product was purified by silica gel column chromatography (5% EtOAc/cyclohexane) to furnish 2-hydroxy-4-pentadecylbenzaldehyde 18 as a white solid (2.45 g, 77%). Mp. 50.6-51.8° C.; IR ($\tilde{v}$/cm$^{-1}$): 2914, 2848, 1667, 1626, 1470, 1306, 1191, 1128, 797, 735; $^1$H NMR (400 MHz, Chloroform-d) δ 11.06 (s, 1H, C2-OH), 9.85 (s, 1H, CHO), 7.46 (d, J=7.8 Hz, 1H, H6), 6.85 (dd, J=7.9, 1.5 Hz, 1H, H5), 6.82 (d, J=1.4 Hz, 1H, H3), 2.63 (t, 2H, H1'), 1.76-1.48 (m, 2H, H2'), 1.40-1.18 (m, 24H, H3'-H14'), 0.89 (t, J=5.7 Hz, 3H, H15') ppm; $^{13}$C NMR (101 MHz, Chloroform-d) δ 195.8 (CHO), 161.8 (C2-OH), 153.8 (C4), 133.6 (C6), 120.5 (C5), 118.8 (C1), 117.1 (C3), 36.4 (C1'), 31.9 (C13'), 30.7 (C2'), 29.7 (6C), 29.6 (1C), 29.5 (1C), 29.4 (1C), 29.3 (1C), 22.7 (C14'), 14.1 (C15') ppm; HRMS (ESI+). Found (M+H)$^+$ 333.2786, $C_{22}H_{37}O_2$ (M+H)$^+$ requires 333.2788. This data is consistent with that reported in the literature. [25]

2-(Hydroxymethyl)-5-pentadecylphenol 19

2-Hydroxy-4-pentadecylbenzaldehyde 18 (0.48 g, 1.44 mmol) was dissolved in 15 mL of freshly distilled dry THF under inert conditions in a 25 ml, round bottom flask. The reaction was cooled 0° C. and LiAlH$_4$ (0.22 g, 5.78 mmol) was carefully added. The reaction was slowly warmed to rt and was stirred for 2 h. Upon completion, the reaction was cooled again to 0° C. and a 2% aq. NaOH (10 mL) was added dropwise to quench the unreacted LiAlH$_4$ followed by dilution with ice-cold water (25 mL). The organic material was the extracted with EtOAc (3×320 mL) and combined organic phases were washed with brine (50 mL), dried over anhydrous $Na_2SO_4$, filtered and the solvent was removed in vacuo to obtain crude product which was then subjected to column chromatography (20% EtOAc/cyclohexane) to obtain 2-(hydroxymethyl)-5-pentadecylphenol 19 as a white crystalline solid (0.39 g, 81%). Mp. 94.6-95.9° C.; IR ($\tilde{v}$/cm$^{-1}$): 3442, 3165, 2915, 2847, 1624, 1592, 1463, 1440, 1284, 1125, 992, 826, 753; $^1$H NMR (400 MHz, Chloroform-d) δ 7.13 (s, 1H, C2-OH), 6.93 (d, J=7.6 Hz, 1H, 1H6), 6.73 (d, J=1.6 Hz, 1H, H3), 6.67 (dd. J=7.6, 1.6 Hz, 1H, H5), 4.83 (s, 2H, CH$_2$OH), 2.54 (t, 2H, H1'), 2.13 (br, s, 1H), 1.68-1.49 (m, 2H, H2'), 1.42-1.17 (m, 24H, H3'-H14'), 0.87 (t, J=5.6 Hz, 3H, H15') ppm; $^{13}$C NMR (101 MHz, Chloroform-d) δ 156.0 (C2), 145.0 (C4), 127.6 (C6), 121.9 (C1), 120.2 (C5), 116.5 (C3), 64.6 (—CH$_2$OH), 35.7 (C1'), 31.9 (C13'), 31.3 (C2)', 29.7 (6C), 29.6 (1C), 29.5 (1C), 29.4 (1C), 29.3 (1C), 22.7 (C14'), 14.1 (C15') ppm; HRMS (ESI+). Found (M+Na)$^+$ 357.2770, $C_{22}H_{38}NaO_2$ (M+Na)$^+$ requires 357.2764. This data was consistent with that reported in the literature. [26]

2-(4,6-Diphenyl-1,3,5-triazin-2-yl)-5-pentadecylphenol 20

A mixture of 2-(hydroxymethyl)-5-pentadecylphenol 19 (0.19 g, 0.57 mmol), benzamidine hydrochloride (0.15 g, 0.97 mmol), $Na_2CO_3$ (0.10 g, 0.97 mmol) and Cu(OAc)$_2$ (10 mol %) was stirred in toluene (3.5 mL) at 110° C. for 24 h. The resulting mixture was cooled to rt and then extracted with EtOAc (3-10 mL) followed by a brine wash. The organic phases were combined and dried over anhydrous $Na_2SO_4$ and evaporated under reduced pressure. The crude product was purified by column chromatography on silica gel (5% EtOAc/cyclohexane) to give 2-(4,6-diphenyl-1,3,5-triazin-2-yl)-5-pentadecylphenol 20 as a white crystalline solid (0.16 g, 62%). Mp. 117.6-119.4° C.; IR ($\tilde{v}$/cm$^{-1}$): 2915, 2849, 1587, 1509, 1470, 1394, 1365, 1352, 1314, 1232, 753, 689; $^1$H NMR (400 MHz, Chloroform-d) δ 13.27 (s, 1H, C1-OH), 8.66 (dd, J=11.2, 7.8 Hz, 6H, H2" and H4"), 7.77-7.49 (m, 5H, H3" and H3), 6.93 (d, J=1.6 Hz, 1H, H6)), 6.89 (dd, J=8.2, 1.7 Hz, 1H, H4), 2.68 (t, 2H, H1'''), 1.77-1.66 (m, 2H, H2'''), 1.41-1.22 (m, 24H, H3'''-H14''') (0.90 (t, J=5.8, 3H, H15''') ppm; $^{13}$C NMR (101 MHz, Chloroform-d) δ 171.9 (C2' and C6'), 162.2 (C1), 151.5 (C5), 135.3 (C1"), 133.0 (C2"), 129.8 (C3), 129.0 (C3"), 128.8 (C4"), 120.1 (C4), 117.7 (C6), 115.2 (C2), 36.2 (C1'''), 31.9 (C13'''), 30.9 (C2'''), 29.7 (6C), 29.6 (1C), 29.5 (1C), 29.4 (1C), 29.3 (1C), 22.7 (C14'''), 14.1 (C15''') ppm; HRMS (ESI+). Found (M+H)$^+$ 536.3643, C % H$_{46}$NO, (M+H)$^+$ requires 536.3636.

2-Hydroxy-4-pentadecylbenzonitrile 22

2-Hydroxy-4-pentadecylbenzaldehyde 18 (1.05 g, 3.15 mmol) and hydroxylamine hydrochloride (0.29 g, 4.10 mmol) were added successively to a solution of anhydrous ferric chloride (0.26 g, 1.58 mmol) in 20 mL dry DMF. The mixture was refluxed for 16 h. After completion of the reaction, the solution was poured into 200 mL water and extract with EtOAc (3-50 mL) and washed several times with water. The combined organic mixture was dried over anhydrous $Na_2SO_4$, concentrated under reduced pressure and the residue was purified by column chromatography on silica gel (20% EtOAc/cyclohexane) to furnish 2-hydroxy-4-pentadecylbenzonitrile 22 as a white solid (0.82 g, 80%). Mp. 71.4-72.9° C.; IR ($\tilde{v}$/cm$^{-1}$): 3273, 2957, 2915, 2851, 2229, 1615, 1585, 1470, 1439, 1310, 949, 874, 796. $^1$H NMR (400 MHz, Chloroform-d) δ 7.42 (d, J=7.9 Hz, 11H, 146), 6.85 (d, J=1.4 Hz, 1H, H3), 6.82 (dd, J=7.9, 1.4 Hz, 1H, H5), 6.64 (s, 1H, C2-OH), 2.61 (t, 3H, H1'), 1.67-1.56 (m, 2H, H2'), 1.35–1.23 (m, 24H, H3'-H14'), 0.89 (t, J=5.6 Hz, 3H, H15') ppm; $^{13}$C NMR (101 MHz, Chloroform-d) δ 158.7 (C2), 151.3 (C4), 132.6 (C6), 121.4 (C5), 116.8 (C1'), 116.4 (C3), 96.5 (C1), 36.2 (C1"), 31.9 (C13"), 30.8 (C2"), 29.7 (6C), 29.6 (1C), 29.4 (1C), 29.4 (1C), 29.2 (1C), 22.7 (C14"), 14.1 (C15") ppm; HRMS. Found (M+Na)$^+$ 352.2605, $C_{22}H_{35}NNaO$ (M+Na)$^+$ requires 352.2611.

6,6',6"-(1,3,5-Triazine-2,4,6-triyl)tris(3-pentadecylphenol) 21

2-Hydroxy-4-pentadecylbenzonitrile 22 (0.37 g, 1.12 mmol) was placed in a microwave reactor tube. The tube was sealed and then subjected to microwave irradiation (200 W, 220° C.) for 3 h. After cooling, the crude product was purified by column chromatography (5% EtOAc/cyclohexane) to afford 6,6',6"-(1,3,5-triazine-2,4,6-triyl)tris(3-pentadecylphenol) 21 as a light yellowish crystalline solid (0.133 g, 73%). Mp. 75.8-77.7° C.; IR ($\tilde{v}$/cm$^{-1}$): 2916, 2848, 1630, 1584, 1535, 1494, 1386, 1361, 1310, 1228, 1161, 799; $^1$H NMR (400 MHz, Chloroform-d) δ 12.98 (s, 1H, C1-OH), 8.04 (d, J=8.2 Hz, 1H, H5), 6.90 (s, 1H, H2), 6.85 (dd, J=8.4, 1.5 Hz, 1H, H4), 2.64 (t, J=7.7 Hz, 2H, H1"), 1.73-1.61 (m, 2H, H2"), 1.40-1.20 (m, 24H, H3"-H14"), 0.89 (t, J=5.6 Hz, 3H, H15"); $^{13}$C NMR (101 MHz, Chloroform-d) δ 169.2 (C2'), 162.8 (C1), 152.9 (C3), 128.7 (C5), 120.7 (C4), 118.1 (C2), 113.4 (C6), 36.2 (C1"), 31.9 (C13"), 30.7 (C2"), 29.7 (6C), 29.6 (1C), 29.5 (1C), 29.4 (1C), 29.4 (1C), 22.7 (C14"), 14.1 (C15"); HRMS: Found (M+H)$^+$, $C_{66}H_{106}N_3O_3$ (M+H)$^+$ requires 988.8229.

3,4-dimethoxybenzohydrazide 24

Palladium on activated charcoal (10 wt %, 645 mg, 0.61 mmol) was added at rt to a stirred suspension of veratraldehyde (2.00 g, 12.0 mmol) and NaOH (1.07 g, 26.4 mmol) in water (48 mL). The mixture was stirred for 20 h at 80° C. and a diminished pressure of 800 mbar. After cooling to rt the mixture was filtered through Celite® and poured onto 1N $H_2SO_4$ (60 mL). The resulting precipitate was collected by filtration and washed with water (120 mL). The filtrate was extracted with EtOAc (3×20 mL) and the combined organic extracts were dried over $Na_2SO_4$. After evaporation of the solvent the resulting solid was combined with the residue of filtration and dried under diminished pressure in order to obtain 3,4-dimethoxybenzoic acid as a colourless solid (1.92 g, 10.5 mmol, 87%). Mp. 178.3-180.1° C.; IR ($\tilde{v}$/cm$^{-1}$): 2964, 2836, 1671, 1516, 1298, 1266, 1232, 1023, 917, 758; $^1$H NMR (300 MHz, Chloroform-d) δ 11.39 (s, 1H, CO$_2$H), 7.79 (dd, J=8.4, 2.0 Hz, 1H, H6), 7.60 (d, J=2.0 Hz, 1H, H2), 6.92 (d, J=8.5 Hz, 1, H5), 3.96 (s, 3H, C4-OCH$_3$), 3.95 (s, 3H, C3-OCH$_3$) ppm; $^{13}$C NMR (76 MHz, Chloroform-d) δ 172.0 (CO$_2$H), 153.7 (C4) 148.7 (C3), 124.6 (C6), 121.7 (C1), 112.3 (C2), 110.3 (C5), 56.1 (C4-OCH$_3$), 56.0 (C3-OCH$_3$) ppm; MS (ESI+): m/z (%)=181.1 (100) [M−H]$^-$. The analytical data are in accordance with the literature, [27] A solution of 3,4-dimethoxybenzoic acid (800 mg, 4.39 mmol) and conc. $H_2SO_4$ (90.0 µL, 1.62 mmol) in EtOH (5 mL) was stirred for 18 h at reflux. After cooling to rt the solvent was evaporated and the residue was dissolved in diethyl ether (15 mL). After washing with saturated NaHCO$_3$ (5 mL) and drying over $Na_2SO_4$ the solvent was evaporated in order to obtain ethyl 3,4-dimethoxybenzoate as a colourless oil (868 mg, 4.13 mmol, 94%), IR ($\tilde{v}$/cm$^{-1}$): 2979, 2839, 1708, 1514, 1345, 1290, 1269, 1177, 1025, 763; $^1$H NMR (300 MHz, Chloroform-d) δ 7.68 (dd, J=8.4, 2.0 Hz, 1H, 116), 7.55 (d, J=2.0 Hz, 1H, H2), 6.88 (d, J=8.4 Hz, 1H, H5), 4.36 (q, J=7.1 Hz, 2H, CH$_2$CH$_3$), 3.93 (s, 6H, C3-OCH$_3$, C4-OCH$_3$), 1.39 (t, J=7.1 Hz, 3H, CH$_2$CH$_3$) ppm; $^{13}$C NMR (76 MHz, Chloroform-d) δ 166.4 (CO$_2$Et), 152.8 (C4) 148.5 (C3), 123.4 (C6), 123.0 (C1), 111.9 (C2), 110.2 (C5), 60.8 (CH$_2$CH$_3$), 56.0 (2C, C3-OCH$_3$, C4-OCH$_3$), 14.4 (CH$_2$CH$_3$) ppm; MS (ESI+): m/z (%)=211.1 (100) [M+H]$^+$, 233.1 (5)

[M+Na]⁺. The analytical data are in accordance with the literature. [28] A solution of ethyl 3,4-dimethoxybenzoate (868 mg, 4.13 mmol.) and hydrazine hydrate (64 wt %, 600 µL, 12.4 mmol) in EtOH (0.3 mL) was refluxed for 18 h while stirring. After cooling to rt the solvent was evaporated and the residue was dissolved in water (10 mL). The resulting solution was extracted with EtOAc (10×10 mL) and the combined organic extracts were dried over $Na_2SO_4$ and evaporated in order to obtain 3,4-dimethoxybenzohydrazide 24 as a colourless solid (770 mg, 3.92 mmol, 95%). Mp. 132.8-134.4° C.; IR ($\tilde{v}/cm^{-1}$): 3307, 2939, 2845, 1626, 1500, 1275, 1148, 1073, 957, 635; ¹H NMR (300 MHz, DMSO-$d_4$) δ 9.62 (s, 1H, NHNH₂), 7.44 (dd, J=8.2, 1.2 Hz, 1H H6), 7.42 (d, J=2.0 Hz, 1H, H2), 6.99 (d, J=8.2 Hz, 1H, H5), 4.42 (s, 2H, NHNH₂), 3.79 (s, 6H, C3-OCH₃, C4-OCH₃) ppm; ¹³C NMR (76 MHz, DMSO-$d_6$) δ 165.5 (CO₂NHNH₂), 151.0 (C4) 148.1 (C3), 125.4 (C1), 120.0 (C6), 110.8 (C5), 110.1 (C2), 55.5 (C3-OCH/C4-OCH), 55.4 (C3-OCH₃/C4-OCH₃) ppm; MS (ESI+): m/z (%)=197.4 (100) [M+H]⁺, 219.3 (22) [M+Na]⁺. The analytical data are in accordance with the literature. [16]

2-[5-(3,4-dimethoxyphenyl)-1,3,4-oxadiazol-2-yl]-5-pentadecylphenol 25

To a stirred solution of 2-hydroxy-4-pentadecylbenzaldehyde (500 mg, 1.51 mmol) in diethyl ether (3.5 mL) and MeOH (3.5 mL) was added 3,4-dimethoxybenzohydrazide 24 (325 mg, 1.66 mmol). The resulting mixture was stirred over night at rt. During that time a colorless solid precipitated which was collected by filtration, washed with cyclohexane/EtOAc=10/1 (30 mL) and dried under reduced pressure. Thus N-[(2-hydroxy-4-pentadecylphenyl) methylidene]-3,4-dimethoxybenzohydrazide 25 was obtained as a colourless solid (623 mg, 1.22 mmol, 82%). Mp. 123.7-125° C.; IR ($\tilde{v}/cm^{-1}$): 3225, 2918, 2849, 1639, 1415, 1271, 1194, 1132, 1022, 771; ¹H NMR (600 MHz, acetone-$d_6$) δ 11.64 (s, 1H, OH), 11.21 (s, 1H, NH), 8.51 (s, 1H, CHN), 7.61 (dd, J=8.3, 2.0 Hz, 1H, H6), 7.57 (d, J=2.0 Hz, 1H, H2), 7.23 (d, J=7.7 Hz, 1H, H6'), 7.06 (d, J=8.4 Hz, 1H, H5), 6.79 (s, 1H, H3'), 6.77 (d, J=7.7 Hz, 1H, H5'), 3.88 (s, 6H, C3-OCH₃, C4-OCH₃), 2.59 (t, J=7.8 Hz, 2H, H1''), 1.62 (q, J=7.8 Hz, 2H, H2''), 1.34-1.23 (m, 24H, H3''-H14''), 0.87 (t. J=6.9 Hz, 3H, H15'') ppm; ¹³C NMR (151 MHz, acetone-16) a 162.2 (CONH), 158.6 (C2'), 152.6 (C4), 149.2 (C3), 149.1 (CHN), 146.9 (C4') 130.7 (C6'), 125.2 (C1), 120.7 (C6), 119.5 (C5'), 116.5 (C3), 115.9 (C1'), 110.9 (C5), 110.8 (C2), 55.2 (2C, C3-OCH₃, C4-OCH₃), 35.6 (C1''), 31.8 (C13''), 31.0 (C2''), 29.5 (6C), 29.4, 29.3, 29.2 (2C), 22.5 (C14''), 13.5 (C5'') ppm; MS (ESI+): m/z (%) 511.7 (100) [M+H]⁺; HRMS (ESI+): Found (M+H)⁺ 511.3514, $C_{31}H_{47}N_2O_4(M+H)^+$ requires 511.3536.

2-[5-(3,4-Dimethoxyphenyl)-1,3,4-oxadiazol-2-yl]-5-pentadecylphenol 23

To a stirred solution of N'-[(2-hydroxy-4-pentadecylphenyl)methylidene]-3,4-dimethoxybenzohydrazide 25 (100 mg, 196 µmol) in dry acetone (4 mL) was added PIDA (126 mg, 392 µmol) under an atmosphere of argon. The resulting mixture was stirred for 2.5 h at rt and another portion of PIDA (63.1 mg, 196 µmol) was added. After stirring further 2.5 h the solvent was evaporated and the residue was purified by column chromatography on silica gel (5-70% EtOAc/cyclohexane) in order to obtain 2-[5-(3,4-dimethoxyphenyl)-1,3,4-oxadiazol-2-yl]-5-pentadecylphenol 23 as a yellowish solid (46.3 mg, 91.0 µmol, 47%). Mp. 106.5-107.9° C.; IR ($\tilde{v}/cm^{-1}$): 2955, 2919, 2850, 1609, 1583, 1503, 1469, 1284, 1229, 1098, 721; ¹H NMR (400 MHz, Chloroform-d) δ 10.12 (s, 1H, OH), 7.75 (d, J=8.0 Hz, 1H, H3), 7.71 (dd, J=8.4, 2.0 Hz, 1H, H6'), 7.64 (d, J=2.0 Hz, 1H, H2'), 7.00 (d, J=8.4 Hz, 1H, H5'), 6.97 (d, J=1.4 Hz, 1H, H6), 6.86 (dd, J=8.0, 1.6 Hz, 1H, H4), 4.01 (s, 3H, C3'-OCH₃), 3.98 (s, 3H, C4'-OCH₃), 2.64 (t, J=7.5 Hz, 2H, H1''), 1.63 (q, J=7.3 Hz, 2H, H2''), 1.33-1.23 (m, 24H, H3''-H14''), 0.88 (t, J=6.8 Hz, 3H, H15'') ppm; ¹³C NMR (101 MHz, Chloroform-d) δ 164.0 (oxadiazole-C2), 163.0 (oxadiazole-C5), 157.6 (C1), 152.3 (C4'), 149.7 (C5), 149.4 (C3'), 128.6 (C6'), 126.2 (C3), 120.4 (C4), 117.2 (C6), 115.9 (C1'), 111.1 (C5'), 109.4 (C2'), 105.8 (C2), 56.2 (C3-OCH₃), 56.1 (C4'-OCH₃), 36.1 (C1''), 31.9 (C13''), 30.9 (C2''), 29.7 (6C), 29.6, 29.5, 29.4, 29.2, 22.7 (C14''), 14.1 (C15'') ppm; MS (ESI+): m/z (%)=509.6 (100) [M+H]⁺; HRMS (ESI+). Found (M+H) 509.3372. $C_{31}H_{45}N_2O_4$ (M+H)⁺ requires 509.3379.

REFERENCES 1 (a) H. C. James and I. D. Fabien, *Introduction to Chemical form biomass,* 2008, John Wiley and Sons. United Kingdom; (b) A. Behr, L. Joluen, *Alternative Feedstocks for Synthesis*, Ch-J. Li Handbook of Green Chemistry, Volume 7: Green Synthesis, first ed., Wiley-VCH. Weinheim, 2012, 69-92.

2 (a) E. M. Serum, S. Selvaknar. N. Zinimermannc, M. P. Sibi, *Green Chem.,* 2 (118, 20, 1448-1454; (b) C. Sze Ki Lin, L. A. Pfaltzgraff. L. Herrero-Davila, E. B. Mubofu, S. Abderrahim, J. H. Clark. A. A. Kontinas, N. Kopsahelis, K. Stamatelatou, F. Dickson, S. Thankappan, Z. Mohamed, R. Brocklesby and R. Luque, *Energy Environ. Sci.,* 2013, 6, 426-464.

3 A. M. Murtala, N. N. Shawal and H. D. Usman, *Int. J. Eng. Sci. and Tech.,* 2012, 4, 721-730.

4 (a) Y. Xu, M. A. Hanna and L. Isom. *The Open Agric. J.,* 2008, 2, 54-61; (b) P. L. Rivilli, G. I. Yranzo and J. D. Perez, *Bio. Resources,* 2011, 6, 2703-2710; (c) F. Jin and H. Enomoto, *Bio. Resources,* 2009, 4, 704-713.

5 Cosmetics: (a) V V. Costa. K. A. da Silva Rocha. L. C. A. Oliveira. E. F. Kozhevnikova, I. V. Kozhevnikovc and E V. Gusevskaya. *RSC Adv.,* 2016, 6, 43217-43222; (b) F. G. Delolo. K. C. B. Oliveira. E. N. dos Santos and E. V. Gusevskaya, *Molecular Catalysis* 2019, 462 1-9; (c) A. L. P. de Meireles. M dos Santos Costa. K. A. da Silva Rocha. E. F. Kozhevikova, I. V. Kozhevnikov and E. V. Gusevskaya *Chem Cat Chem,* 2014, 6, 2706-2711. Chemicals and pharmaceuticals: (a) A. Corma, S. Iborra and A. Velty. *Chem. Rev.* 2007, 107, 2411; (b) T. A. Bender. J. A. Dabrowski and M. R. Gagne. *Nature Reviews Chemistry* 2018, 35-46; (c) S. Bander, P. E. Podsiadly. D. J. Cole-Hamilton and L. J. Goossen, *Green Chemistry,* 2014, 16, 4885-4890.

6 (a) See for example (i) D. Stubba, G. Lahm, M. Geffe, J. W. Runyon. A. J. Arduengo III and Till Opatz, *Angew. Chem. Int. Ed.* 2015, 54, 14187-14189; (ii) J. Kühlborn, A.-K. Danner, H. Frey, R. Iyer, A. J. Arduengo, III and Till Opatz, *Green Chem.,* 2017, 19, 3780-3786; (b) See for example (i) J. A. Mmongoyo, Q. A. Mgani, S. J. M. Mdachi. P. J. Pogorzelec and D. J. Cole-Hamilton, *Eur. J. Lipid Sci. Technol.* 2012, 114, 1183-1192: (ii) C. Voirin, S. Caillol, N. V. Sadavarte. B. V. Tawade, B. Boutevin and P. P. Wadgaonk, *Polym. Chem,* 2014, 5, 3142-3162; (iii) S. Caillol, *Current Opinion in Green and Sustainable Chemistry* 2018, 14:26-32; (iv) M. Hemshckhar, M. S. Santhosh, K. Kemparaju and K. S. Girish, *Basic & Clinical Pharmacology & Toxicology,* 2011, 110, 122-132; (v) V. S. Balachandran S. R. Jadhav. P. Kunar Veimula and G. John, *Chem. Soc. Rev.,* 2013, 42, 427-427.

7 I. Kubo, H. Muroi and M. Himejima, *J. Agric. Food Chem.,* 1993, 41, 1016-1019; M. S. C. Oliveira, S. M. Morais, D. V. Magalhães, W. P. Batista, I. G. P. Vieira, A. A. Craveiro, J. E. S. A Menezes, A. F. U. Carvalho and G. P. G. Lima, *Acta. Trop,* 2010, 117, 165-170; Y. Wu, L. He, L. Zhang, J. Chen. Z. Yi, J. Zhang, M. Liu and X. Pang, *J. Pharmacol. Exp. Ther.,* 2011, 339, 403-411.

8 P. G. Parejo, M. Zayata and D. Levy, *J. Mater. Chem.,* 2006, 16, 2165.2169.

9 (a) D. L. Giokas. A. Salvador and A. Chisvert, *Trends Anal Chem.,* 2007, 26, 360-374; (b) B. A. M. C. Santosa, A. C. P. da Silva, M. L. Bello. A. S. Gonçalves, T. A. Gouvêa, R. F. Rodrigues. L. M. Cabral, C. R. Rodrigues, *Journal of Photochemistry and Photobiology A: Chemistry,* 2018, 356, 219-229.

10 M. Zayat, P. G. Parejo and D. Levy, *Chem. Soc. Rev.,* 2007, 36, 1270-1281.

11 A. Maliakal, G. Lem, N. J. Turro, R. Ravichandran. J. C. Suhadolnik, A. D. DeBellis. M. G. Wood and J. Lau, *J. Phys. Chen.* A, 2002, 106, 7680-7689; P. F. McGarry, S. Jockusch, Y. Fujiwara, N. A. Kaprindis and N. J. Turro, *J. Phys. Chem. A,* 1997, 101, 764-767.

12 (a) Sunscreens: K. Morabito, N. C. Shapley, K. G. Steeley and A. Tripathi, *International Journal of Cosmetic Science,* 2011, 33, 385-390; (b) Steinberg, D. C. (2005) Regulations of sunscreens worldwide. In Sunscreens (Edited by N. A. Shaath), pp. 173-198. Taylor & Francis. Boca Raton, FL 13 P. Gago-Fenero, M. S. Diaz-Cruz and D. Barceló. *Anal. Bioanal. Chem.,* 2012, 404:2597-2610.

14 (a) M. Mosquera. J. C. Penedo, M. C. R. Rodriguez and F. Rodriguez-Prieto, *J. Phys. Chem.,* 1996, 100, 5398-5407; (b) G. Woessner, G. Goelier, P. Kollat, J. J. Stezowski, M. Hauser, U. K. A. Klein and H. E. A. Kramer, *J. Phys. Chem.,* 1984, 88, 5544-5550; (d) W. Klöpffer, *Adv. Photochem.,* 1977, 10, 311-358.

15 K. G. Rutherford, W. Redmond and C. S. B. Rigamonti, C. S. B., *J. Org. Chem,* 1961 26, 5149-5152.

16 B. Narasimhan. S. Ohlan, R. Ohlan, V. Judge and R. Narang, *Eur. J. Med. Chem.* 2009, 44, 689-700.

17 H. M. Chawla, N. Pant, S. Kumar, S. Mrig. B. Srivastava, N. Kumar and D. StC. Black, *J. Photochemistry and Photobiology B: Biology,* 2011, 105, 25-33.

18 R. A. Sheldon, *Current Opinion in Green and Sustainable Chemistry* 2019, 18, 13-19.

19 R. A. Sheldon and J. M. Woodley. *Chem. Rev.* 2018, 118, 801-838

20 N. S. Reddy, A. S. Rao, M. A. Chari, V. R. Kumar, V. Jyotly, V. Himabindu, *Lett. Org. Chem.* 2012, 9, 287-293.

21 R. Zehnter. H. Gerlach, *Liebigs Annalen* 1995, 1995, 2209-2220.

22 D. L. J. Clive, A. Khodabocus. P. G. Vernon, A. G. Angoh, L Bordeleau, D. S. Middleton, C. Lowe, D. Kellner, *J. Chem. Soc., Perkin Trans,* 1 1991, 1433-1444.

23 K. K. Julich-Gruner, O. Kataeva, A. W. Schmidt, H. J., Knölker. *Chem. Eur. J.* 2014, 20, 8536-8540.

24 R. Bernini, S. Cacchi, I. De Salve, G. Fabrizi, *Synthesis,* 2007, 6, 873-882.

25 P. Payne, J. H. P. Ty man. S. K. Mehet and A Ninagawa, *J. Chem. Res.* 2006, 402-405.

26 J. H. P. Tyman and S. K. Mehet, *Chem. and Phys. of Lipids,* 2003, 126, 177-199.

27 G. W. Perold, L. Carlton, A. S. Howard, J. P. Michael, *J. Chem. Soc., Perkin Trans,* 1 1988, 881-884.

28 B. Teng. J. Shi. C. Yao, *Green Chem,* 2018, 20, 2465-2471.

The invention claimed is:

1. A compound having excited state intramolecular proton transfer (ESIPT) character, said compound being at least one selected from the group consisting of:

(i).

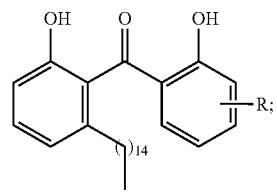

(ii).

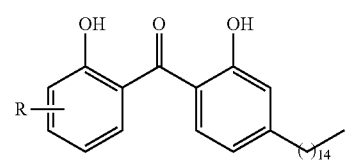

(iii).

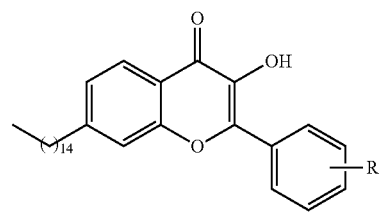

(iv).

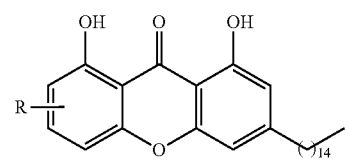

(v).

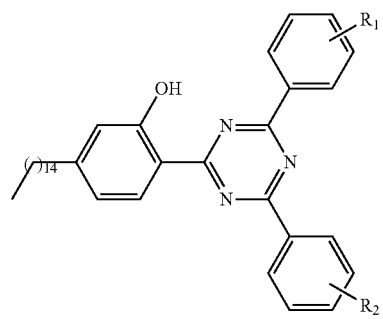

(vi).

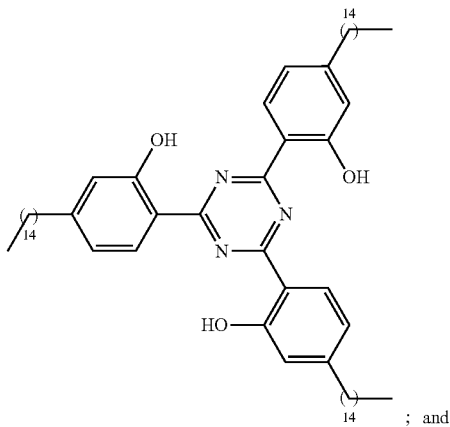

(vii).

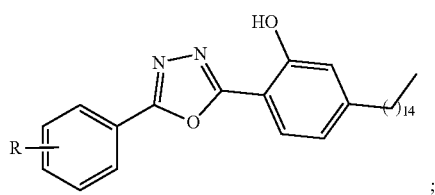

;

wherein for compounds (i) to (vii) R and/or $R_1$ and/or $R_2$ may each be at least one substituent or moiety located at one or more of an ortho, meta and/or para position on the benzene ring and may be selected from the group consisting of: hydrogen, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, thioalkyl, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, nitrile, silyl, sulfenyl, sulfinyl, sulfonyl, haloalkyl, haloalkoxy, trihalomethanesulfonyl, trihalomethanesulfonamido, an amino, a mono-substituted amino, a di-substituted amino group, esters, alcohol, acetates, and protected derivatives of any one of the aforementioned.

2. A method for the treatment and/or prevention of sunburn in a human or animal body, comprising applying the at least one compound of claim 1 to the human or animal body.

3. The method according to claim 2, comprising formulating any one or more of compounds (i)-(vii) into compositions, and wherein the compositions include at least one selected from the group consisting of: aqua, glycerine, trisodium ethylene diamine tetra-acetic acid (EDTA), tocopheryl acetate, phenoxyethanol, cetyl alcohol, xantham gum, polyethylene glycol (PEG), sodium cetearyl sulphate, glycerol stearate, and parfum.

* * * * *